United States Patent
Boyd et al.

(10) Patent No.: US 7,879,885 B2
(45) Date of Patent: Feb. 1, 2011

(54) THIOALKENEAMIDES AS TRANSKETOLASE INHIBITORS

(75) Inventors: Steven A. Boyd, Longmont, CO (US); Kevin R. Condroski, Broomfield, CO (US); Allen Thomas, Louisville, CO (US); Stephen S. Gonzales, Media, PA (US); Indrani W. Gunawardana, Longmont, CO (US); Yvan Le Huerou, Boulder, CO (US); Todd T. Romoff, Firestone, CO (US); Francis X. Sullivan, Boulder, CO (US)

(73) Assignee: Array Biopharma, Inc., Boulder, CO (US)

( * ) Notice: Subject to any disclaimer, the term of this patent is extended or adjusted under 35 U.S.C. 154(b) by 935 days.

(21) Appl. No.: 10/593,911

(22) PCT Filed: Mar. 23, 2005

(86) PCT No.: PCT/US2005/009966

§ 371 (c)(1),
(2), (4) Date: May 11, 2007

(87) PCT Pub. No.: WO2005/095344

PCT Pub. Date: Oct. 13, 2005

(65) Prior Publication Data

US 2007/0293501 A1     Dec. 20, 2007

Related U.S. Application Data

(60) Provisional application No. 60/556,218, filed on Mar. 24, 2004.

(51) Int. Cl.
*A61K 31/44* (2006.01)

(52) U.S. Cl. .......................... 514/357; 546/6; 546/329

(58) Field of Classification Search ................. 546/329
See application file for complete search history.

(56) References Cited

U.S. PATENT DOCUMENTS 5,466,811 A  11/1995 Alexander
6,451,341 B1  9/2002 Slaga et al.

FOREIGN PATENT DOCUMENTS

GB    924 539 A    4/1963
JP    06-041181 A    2/1994

OTHER PUBLICATIONS

M. Cascante, et al., "Role of Thiamin (Vitamin B-1) and Transketolase in Tumor Cell Proliferation," Nutrition and Cancer, vol. 36, No. 2, pp. 150-154 (2000).
F. Hayakawa, et al., "Isolation and Characterization of a Coupled Compound of Thiamin with Catechol," Journal of Nutritional Science and Vitaminology, vol. 30, pp. 327-334 (1984).
C.-Q. Sun, et al., "A General Synthesis of Dioxolenone Prodrug Moieties," Tetrahedron Letters 43, pp. 1161-1164 (2002).
X. Sun, et al., "Synthesis and Evaluation of Oxodioxolenylmethyl Carbamate Prodrugs of Pseudomycins," J. Med. Chem. 44, pp. 2671-2674 (2001).

*Primary Examiner*—James O Wilson
*Assistant Examiner*—Brian McDowell
(74) *Attorney, Agent, or Firm*—Henry D. Coleman; R. Neil Sudol; William J. Sapone

(57) ABSTRACT

The present invention provides thioalkeneamides of formula (I) which are useful as transketolase inhibitors: wherein $R^1$, $R^2$, $R^3$, $R^4$, $R^5$, $R^6$, $R^a$-$R^d$, n and ring A are as defined herein. The present invention also provides pharmaceutical compositions comprising the compounds of formula (I). The invention provides methods for inhibiting transketolase activity, reducing cellular ribose-5-phosphate levels, inhibiting nucleic acid synthesis, inhibiting cell proliferation and tumor cell growth in vitro and in vivo, stimulating apoptosis in tumor cells and treating cancer by administering a compound of formula (I) or a pharmaceutical composition thereof.

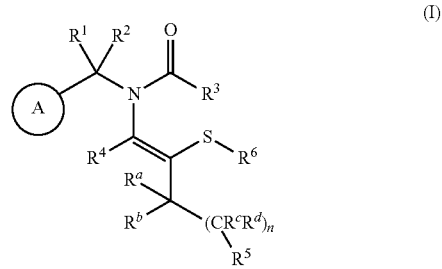

(I)

13 Claims, No Drawings

THIOALKENEAMIDES AS TRANSKETOLASE INHIBITORS

CROSS-REFERENCE TO RELATED APPLICATIONS

This application is a National Phase filing under 35 U.S.C. §371 of International Application PCT/US2005/009966, filed Mar. 23, 2005, which designates the United States, is published in English, and claims benefit under 35 U.S.C. §119(e) of U.S. Provisional Application Ser. No. 60/556,218 filed Mar. 24, 2004. The entire disclosures of these applications are incorporated herein by reference.

FIELD OF THE INVENTION

The present invention relates to thioalkeneamides useful as transketolase inhibitors. The invention provides methods of using these compounds or pharmaceutical compositions comprising these compounds to inhibit transketolase activity. The invention further provides methods of utilizing these compounds or pharmaceutical compositions in the treatment and prevention of cancer.

BACKGROUND OF THE INVENTION

Advanced cancer patients are often deficient in, and their diets thus supplemented with, thiamine (vitamin B1), which is also a common additive in Western world foods as mammals lack the ability to synthesize thiamine. Thiamine is converted to thiamine pyrophosphate (TPP) which is a necessary cofactor for transketolase, a key enzyme in non-oxidative pentose phosphate pathways which shunt carbon away from glycolytic intermediates and form ribose-5-phosphate for increased nucleic acid biosynthesis. Such pathways are often stimulated in situations of active cell proliferation, such as in tumor cells, where lack of oxygen can stimulate non-oxidative pathways which further deprive cells of reducing compounds (e.g., NADP) required for many normal cellular functions. Transketolase has been postulated to be a useful target for the development of anti-cancer therapies which inhibit nucleic acid biosynthetic pathways.

Reported transketolase inhibitors include oxythiamine, 3-[(2-amino-6-methyl-3-pyridinyl)methyl]-5-(2-hydroxyethyl)-4-methyl thiazolium chloride ($N^3PT$), and 3-[(4-amino-2-methyl-5-pyrimidinyl)methyl]-5-(2-hydroxyethyl)-4-methyl 2(3H)-thiazolone chloride (thiamine thiazolone). There is a need to find new transketolase inhibitors, especially TPP-related compounds that are selective inhibitors for transketolase (i.e., which at a selected concentration inhibit transketolase more than other TPP-utilizing enzymes).

SUMMARY OF THE INVENTION

The present invention provides compounds that are transketolase inhibitors and therefore are useful in reducing cellular ribulose/ribose-5-phosphate levels, inhibiting nucleic acid synthesis and cell proliferation, increasing apoptosis in tumor cells and in reducing tumor growth. These compounds have the general formula I:

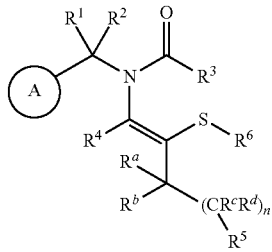

wherein $R^1$, $R^2$, $R^3$, $R^4$, $R^5$, $R^6$, $R^a$-$R^d$, n and ring A are as defined herein. The compounds of this invention may also be in the form of pharmaceutically acceptable derivatives such as salts, esters, or salts of esters.

The invention also provides pharmaceutical compositions comprising the present compounds, and methods for using the present compounds or pharmaceutical compositions. The invention provides methods for inhibiting transketolase activity, reducing cellular ribose-5-phosphate levels, inhibiting nucleic acid synthesis, inhibiting cell proliferation and tumor cell growth in vitro and in vivo, and stimulating apoptosis in tumor cells by administering a compound of the present invention or a pharmaceutical composition comprising a present compound, either alone or in combination with thiamine-restricted diet and/or other therapeutic agents.

DETAILED DESCRIPTION OF THE INVENTION

The present invention features a compound of formula I:

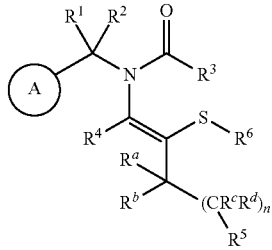

or a pharmaceutically acceptable derivative thereof, wherein:
ring A is a heteroaryl selected from

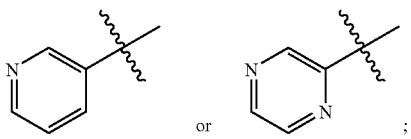

each $R^1$ and $R^2$ is independently H, alkyl, or fluoroalkyl;
$R^3$ is H, alkyl, fluoroalkyl, aralkyl, carbocyclylalkyl, heterocyclyl, carbocyclyl, heterocyclylalkyl, aryl, heteroaryl, heteroaralkyl, —C(O)R, —OR, —$(CH_2)_{1-6}$OR, —$(CH_2)_{1-6}$N(R)$_2$, —N(R)$_2$, or —C(H)(OR)R;
$R^4$ is H, alkyl, fluoroalkyl, —$CO_2$R, —CON(R)$_2$, carbocyclyl, carbocyclylalkyl, heteroaryl or heterocyclyl;
$R^5$ is —$OR^7$ or —$NR^8R^9$;

$R^6$ is —C(O)R, —C(S)R, —C=C—C(O)R, —SR, —S—W—$OR^7$, M, or Y;

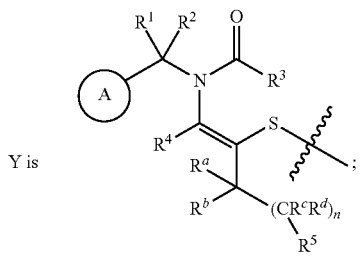

$R^7$ is $R^o$, —C(O)R, —C(O)N(R)$_2$, —C(O)OR, —(CH$_2$)$_{1-6}$—C(O)R, —PO$_3$M$_x$, —P(O)(alkyl)OM', —(PO$_3$)$_2$M$_y$, carbocyclyl, aryl, heterocyclyl, heteroaryl, carbocyclylalkyl, aralkyl, heterocyclylalkyl, heteroaralkyl, or a tumor-targeting moiety;

x is 1 or 2;

y is 1, 2 or 3;

each M is independently H, Li, Na, K, Mg, Ca, Mn, Co, Ni, Zn, or alkyl;

M' is H, Li, Na, K, or alkyl;

$R^8$ is H or alkyl;

$R^9$ is H, alkyl, —C(O)R, —C(O)N(R)$_2$, —C(O)OR, —SO$_2$R, —SO$_2$N(R)$_2$, carbocyclyl, aryl, heterocyclyl, heteroaryl, carbocyclylalkyl, aralkyl, heterocyclylalkyl, heteroaralkyl or a tumor targeting moiety;

each $R^a$ and $R^b$ is independently H, $OR^o$, alkyl, or fluoroalkyl;

each $R^c$ and $R^d$ is independently H, alkyl, or fluoroalkyl;

n is 0-4;

W is alkylene, arylene, heteroarylene, carbocyclylene, or heterocyclylene;

$R^o$ is H or alkyl; and

R is $R^o$, carbocyclyl, aryl, heterocyclyl, heteroaryl, carbocyclylalkyl, aralkyl, heterocyclylalkyl, or heteroaralkyl.

As used herein, the following definitions shall apply unless otherwise indicated. The phrase "optionally substituted" is used interchangeably with the phrase "substituted or unsubstituted" or with the term "(un)substituted." Unless otherwise indicated, the term "alkyl", "carbocyclyl", "heterocyclyl", "aryl", or "heteroaryl", alone or in combination with any other term, may be an optionally substituted group. Such an optionally substituted group may have a substituent at each substitutable position of the group, and each substitution is independent of the other.

The term "alkyl", alone or in combination with any other term, refers to a C$_{1-12}$ straight or branched acyclic hydrocarbon radical that is either completely saturated or contains one or more units of unsaturation. Preferably, an alkyl radical contains from one to six carbon atoms. More preferably, an alkyl radical contains from one to four carbon atoms. A C$_{2-12}$ linear or branched alkyl radical having at least one carbon-carbon double bond is also referred to as "alkenyl". The double bond(s) of the unsaturated hydrocarbon chain may be in either the cis or trans configuration and may occur in any stable point along the chain. A C$_{2-12}$ linear or branched alkyl having at least one carbon-carbon triple bond is also referred to as "alkynyl". The triple bond(s) in an alkynyl radical may occur in any stable point along the chain. The terms "alkoxy", "hydroxyalkyl", "alkoxyalkyl", and "alkoxycarbonyl", alone or in combination with any other term, include both straight and branched hydrocarbon chains. The term "hydroxyalkyl" refers to alkyl substituted with hydroxy.

Examples of alkyl radicals include, but are not limited to, methyl, ethyl, n-propyl, isopropyl, n-butyl, isobutyl, sec-butyl, tert-butyl, pentyl, isoamyl, n-hexyl, ethenyl, propenyl, isopropenyl, butenyl, isobutenyl, pentenyl, hexenyl, hexadienyl, ethynyl, propynyl, butynyl, pentynyl and the like.

The term "alkylene" refers to a divalent alkyl group. Examples of alkylene include, but are not limited to, methylene, ethylene, n-heptylene, 1,3-octylene and the like.

The term "alkoxy" refers to an alkyl ether radical (—O-alkyl). Examples of alkoxy radicals include, but are not limited to, methoxy, ethoxy, n-propoxy, isopropoxy, n-butoxy, isobutoxy, sec-butoxy, tert-butoxy and the like.

The term "cycloalkyl", "carbocyclyl", "carbocyclic", "carbocycle", or "carbocyclo", alone or in combination with any other term, refers to a monocyclic or polycyclic non-aromatic hydrocarbon ring radical having three to twenty carbon atoms, preferably from three to twelve carbon atoms, and more preferably from three to ten carbon atoms. A cycloalkyl, carbocyclyl, carbocyclic, carbocycle, or carbocyclo radical is either completely saturated or contains one or more units of unsaturation but is not aromatic. The unsaturation, if present, may occur in any point in the ring that may result in any chemically stable configuration. The term "cycloalkyl", "carbocyclyl", "carbocyclic", "carbocycle", or "carbocyclo" also includes hydrocarbon rings that are fused to one or more aromatic rings, such as in tetrahydronaphthyl, where the radical or point of attachment is on the non-aromatic ring. The term "carbocyclylalkyl" refers to an alkyl group substituted by a carbocycle.

Unless otherwise indicated, the term "cycloalkyl", "carbocyclyl", "carbocyclic", "carbocycle", or "carbocyclo" also includes each possible positional isomer of a non-aromatic hydrocarbon radical, such as in 1-decahydronaphthyl, 2-decahydronaphthyl, 1-tetrahydronaphthyl and 2-tetrahydronaphthyl. Examples of suitable cycloalkyl groups include, but are not limited to, cyclopropyl, cyclobutyl, cyclopentyl, cyclohexyl, cyclohexenyl, decahydronaphthyl, tetrahydronaphthyl and the like.

The term "carbocyclylene" refers to a divalent carbocyclyl group. Examples of carbocyclylene groups include, but are not limited to, cyclopropylene, cyclobutylene, cyclopentylene, cyclohexylene, and the like.

The term "halogen" or "halo" refers to fluorine (F), chlorine (Cl), bromine (Br), or iodine (I).

The term "aryl", alone or in combination with any other term, refers to an aromatic monocyclic or polycyclic hydrocarbon ring radical containing five to twenty carbon atoms, preferably from six to fourteen carbon atoms, and more preferably from six to ten carbon atoms. Also included within the scope of the term "aryl", as it is used herein, is a group in which an aromatic hydrocarbon ring is fused to one or more non-aromatic carbocyclic or heteroatom-containing rings, such as in an indanyl, phenanthridinyl or tetrahydronaphthyl, where the radical or point of attachment is on the aromatic hydrocarbon ring.

Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. The term "aralkyl" refers to an alkyl group substituted by an aryl. Examples of aralkyl groups include, but are not limited to, benzyl and phenethyl.

The term "arylene" refers to a divalent aryl group. Examples of arylene groups include, but are not limited to, phenylene, naphthylene and the like.

The term "heterocycle", "heterocyclic", or "heterocyclyl", alone or in combination with any other term, refers to a non-aromatic monocyclic or polycyclic ring radical containing three to twenty carbon atoms, preferably three to seven carbon atoms if monocyclic and eight to eleven carbon atoms if bicyclic, and in which one or more ring carbons, preferably one to four, are each replaced by a heteroatom such as N, O, and S. A heterocycle, heterocyclic, or heterocyclyl ring may be fully saturated or may contain one or more units of unsaturation but is not aromatic. The unsaturation, if present, may occur in any point in the ring that may result in any chemically stable configuration. The heterocyclic ring may be attached at a carbon or heteroatom that results in the creation of a stable structure. Preferred heterocycles include 5-7 membered monocyclic heterocycles and 8-10 membered bicyclic heterocycles.

Also included within the scope of the term "heterocycle", "heterocyclic", or "heterocyclyl" is a group in which a non-aromatic ring is fused to one or more aromatic rings, such as in an indolinyl, chromanyl, phenanthridinyl or tetrahydroquinolinyl, where the radical or point of attachment is on the non-aromatic ring. Unless otherwise indicated, the term "heterocycle", "heterocyclic", or "heterocyclyl" also includes each possible positional isomer of a heterocyclic radical, such as in 1-decahydroquinoline, 2-decahydroquinoline, 3-decahydroquinoline, 4-decahydroquinoline, 5-decahydroquinoline, 6-decahydroquinoline, 7-decahydroquinoline, 7-decahydroquinoline, 8-decahydroquinoline, 4a-decahydroquinoline, 8a-decahydroquinoline, 1-indolinyl, 2-indolinyl, 3-indolinyl, 1-tetrahydroquinoline, 2-tetrahydro-quinoline, 3-tetrahydroquinoline and 4-tetrahydro-quinoline. The term "heterocyclylalkyl" refers to an alkyl group substituted by a heterocyclyl.

Examples of heterocyclic groups include, but are not limited to, imidazolinyl, 2,3-dihydro-1H-imidazolyl, imidazolidinyl, indazolinolyl, perhydropyridazyl, pyrrolinyl, pyrrolidinyl, 4H-pyrazolyl, piperidinyl, pyranyl, pyrazolinyl, piperazinyl, morpholinyl, thiamorpholinyl, thiazolidinyl, thiamorpholinyl, oxopiperidinyl, oxopyrrolidinyl, azepinyl, tetrahydrofuranyl, oxoazepinyl, tetrahydropyranyl, thiazolyl, dioxolyl, dioxinyl, oxathiolyl, benzodioxolyl, dithiolyl, dithiolanyl, tetrahydrothiophenyl, sulfolanyl, dioxanyl, dioxolanyl, tetahydrofurodihydrofuranyl, dihydropyranyl, tetrahydropyranodihydrofuranyl, tetrahydrofurofuranyl, tetrahydropyranofuranyl, diazolonyl, phthalimidinyl, benzoxanyl, benzopyrrolidinyl, benzopiperidinyl, benzoxolanyl, benzothiolanyl and benzothianyl.

The term "heterocyclylene" refers to a divalent heterocyclyl group. Examples of heterocyclylene groups include, but are not limited to, tetrahydrofuranylene, pyrrolinylene, pyrrolidinylene and the like.

The term "heteroaryl", alone or in combination with any other term, refers to an aromatic monocyclic or polycyclic ring radical containing five to twenty carbon atoms, preferably five to ten carbon atoms, in which one or more ring carbons, preferably one to four, are each replaced by a heteroatom such as N, O, and S. Preferred heteroaryl groups include 5-6 membered monocyclic heteroaryls and 8-10 membered bicyclic heteroaryls.

Also included within the scope of the term "heteroaryl" is a group in which a heteroaromatic ring is fused to one or more aromatic or non-aromatic rings where the radical or point of attachment is on the heteroaromatic ring. Examples include, but are not limited to, pyrido[3,4-d]pyrimidinyl, 7,8-dihydro-pyrido[3,4-d]pyrimidine and 5,6,7,8-tetrahydro-pyrido[3,4-d]pyrimidine. Unless otherwise indicated, the term "heteroaryl" also includes each possible positional isomer of a heteroaryl radical, such as in 2-pyrido[3,4-d]pyrimidinyl and 4-pyrido[3,4-d]pyrimidinyl. The term "heteroaralkyl" refers to an alkyl group substituted by a heteroaryl.

Examples of heteroaryl groups include, but are not limited to, imidazolyl, quinolyl, isoquinolyl, indolyl, indazolyl, pyridazyl, pyridyl, pyrrolyl, pyrazolyl, pyrazinyl, quinoxalyl, pyrimidinyl, pyridazinyl, furyl, thienyl, triazolyl, thiazolyl, carbazolyl, carbolinyl, tetrazolyl, benzofuranyl, oxazolyl, benzoxazolyl, isoxozolyl, isothiazolyl, thiadiazolyl, furazanyl, oxadiazolyl, benzimidazolyl, benzothienyl, quinolinyl, benzotriazolyl, benzothiazolyl, isoquinolinyl, isoindolyl, acridinyl and benzoisoxazolyl.

The term "heteroarylene" refers to a divalent heteroaryl group. Examples of heteroarylene groups include, but are not limited to, imidazolylene, quinolylene, pyridazylene, pyridylene, pyrazinylene, thiazolylene and the like.

The term "heteroatom" means nitrogen, oxygen, or sulfur and includes any oxidized form of nitrogen such as N(O) [$N^+$—$O^-$], of sulfur such as S(O) and S(O)$_2$, and the quaternized form of any basic nitrogen. Suitable substituents on a substitutable ring nitrogen include alkyl, —N(R')$_2$, —C(O) R', —CO$_2$R', —C(O)C(O)R', —C(O)CH$_2$C(O)R', —SO$_2$R', —SO$_2$N(R')$_2$, —C(=S)N(R')$_2$, —C(=NH)—N(R')$_2$, and —NR'SO$_2$R'; wherein R' is hydrogen, alkyl, phenyl (Ph), —OPh, —CH$_2$Ph, wherein said alkyl or phenyl is optionally substituted by one or more groups independently chosen from alkyl, amino, alkylamino, dialkylamino, aminocarbonyl, halo, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, hydroxyalkyl, haloalkoxy, and haloalkyl.

Unless otherwise indicated, an aryl (including the aryl moiety in aralkyl, aralkoxy, aryloxyalkyl and the like) or heteroaryl (including the heteroaryl moiety in heteroaralkyl and heteroarylalkoxy and the like) group may contain one or more substituents. Examples of such suitable substituents on the unsaturated carbon atom of an aryl or heteroaryl group include halo, —CF$_3$, —OCF$_3$, —OR$^†$, —SR$^†$, —SCF$_3$, —R$^†$, methylenedioxy, ethylenedioxy, —NO$_2$, —CN, —N(R$^†$)$_2$, —NR$^†$C(O)R$^†$, —NR$^†$C(O)N(R$^†$)$_2$, —NR$^†$C(S)N (R$^†$)$_2$, —NR$^†$CO$_2$R$^†$, —NR$^†$NR$^†$C(O)R$^†$, —NR$^†$NR$^†$C(O)N (R$^†$)$_2$, —NR$^†$NR$^†$CO$_2$R$^†$, —C(O)C(O)R$^†$, —C(O)CH$_2$C(O) R$^†$, —CO$_2$R$^†$, —O—C(O)R$^†$, —C(O)R$^†$, —C(O)N(R$^†$)$_2$, —OC(O)N(R$^†$)$_2$, —S(O)$_t$R$^†$, —S(O)$_t$—OR$^†$, —SO$_2$N(R$^†$)C (O)R$^†$, —NR$^+$SO$_2$N(R$^†$)$_2$, —NR$^+$SO$_2$R$^†$, —C(=S)N(R$^†$)$_2$, —C(=NH)—N(R$^†$)$_2$, —C(=N—OR$^†$)—N(R$^†$)$_2$, —O—(CH$_2$)$_{0-6}$—SO$_2$N(R$^†$)$_2$, —(CH$_2$)$_{1-6}$NHC(O)R$^†$, —SO$_2$N(R$^†$)$_2$, —(CH$_2$)$_{1-6}$—OR$^†$, —(CH$_2$)$_{1-6}$—SR$^†$, —(CH$_2$)$_{1-6}$—CN, —(CH$_2$)$_{1-6}$—N(R$^†$)$_2$, —(CH$_2$)$_{1-6}$CO$_2$R$^†$, —C(O)N(R$^†$) N(R$^†$)$_2$, —C(O)N(R$^†$)OH, —C(O)N(R$^†$)SO$_2$R$^†$, —S(O)$_t$N (R$^†$)OR$^†$, and —(CH$_2$)$_{1-6}$—C(O)R$^†$, wherein the two R$^†$s on the same nitrogen optionally taken together form a 5-8 membered saturated, partially saturated or aromatic ring having additional 0-4 ring heteroatoms selected from oxygen, nitrogen and sulfur.

Each R$^†$ is independently selected from R$^‡$, —C(O)R$^‡$, or —S(O)$_t$R$^‡$, wherein each member of R$^†$ except H is optionally substituted by one or more groups chosen from R$^‡$, —OR$^‡$, N(R$^‡$)$_2$, =O, =S, halo, —CF$_3$, —NO$_2$, —CN, —C(O)R$^‡$, —CO$_2$R$^‡$, —C(O)-aryl, —C(O)-heteroaryl, —O-aryl, aralkyl, —S(O)$_t$-aryl, —NR$^‡$SO$_2$R$^‡$, —NR$^‡$C(O)R$^‡$, —NR$^‡$C(O)N(R$^‡$)$_2$, —N(R$^‡$)C(S)N(R$^‡$)$_2$, —NR$^‡$CO$_2$R$^‡$, —NR$^‡$NR$^‡$C(O)R$^‡$, —NR$^‡$NR$^‡$C(O)N(R$^‡$)$_2$, —NR$^‡$NR$^‡$CO$_2$R$^‡$, —C(O)C(O)R$^‡$, —C(O)CH$_2$C(O)R$^‡$, —C(O)N(R$^‡$)N(R$^‡$)$_2$, —C(O)N(R$^‡$)$_2$, —C(O)NR$^‡$SO$_2$R$^‡$, —OC(O)N(R$^‡$)$_2$, —S(O)$_t$R$^‡$, —NR$^‡$SO$_2$N(R$^‡$)$_2$, and —SO$_2$N(R$^‡$)$_2$ wherein the two R$^‡$s on the same nitrogen optionally taken together form a 5-8 membered saturated, partially saturated or aromatic ring having additional 0-4 ring heteroatoms selected from oxygen, nitrogen, and sulfur. Each R‡ is independently H, unsubstituted alkyl, unsubstituted carbocyclyl, unsubstituted aryl, unsubstituted heteroaryl, unsubstituted heterocyclyl, unsubstituted carbocyclylalkyl, unsubstituted aralkyl, unsubstituted heteroaralkyl, or unsubstituted heterocyclylalkyl; and each t is independently 1 or 2.

Unless otherwise indicated, an alkyl (including the alkyl moiety in aralkyl, aralkoxy, aryloxyalkyl, carbocyclylalkyl and the like), carbocyclyl (including the carbocyclyl moiety in carbocyclylalkyl) or heterocyclic group may contain one or more substituents. Examples of such suitable substituents on the saturated carbon of an alkyl or of a carbocyclic or heterocyclic ring include those listed above for the unsaturated carbon of an aryl or heteroaryl group and the following: =O, =S, =NNHR†, =NN(R†)$_2$, =N(CN), =NNHC(O)R†, =NNHCO$_2$(alkyl), =NNHSO$_2$(alkyl), or =NR†.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all endo or exo, cis or trans isomers as well as all stereochemical forms of the structure, i.e., the R and S configurations for each asymmetric center. Therefore, racemates and racemic mixtures, single enantiomers, diastereomeric mixtures and individual diastereoisomers of the present compounds are expressly included within the scope of the invention. Although the specific compounds exemplified herein may be depicted in a particular stereochemical configuration, compounds having either the opposite stereochemistry at any given chiral center or mixtures thereof are also envisioned.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are also within the scope of this invention.

It will be apparent to one skilled in the art that certain compounds of this invention may exist in alternative tautomeric forms. All such tautomeric forms of the present compounds are within the scope of the invention. Unless otherwise indicated, the representation of either tautomer is meant to include the other.

Certain embodiments of the present invention are compounds represented by formulae IIa, IIb, IIc and IId:

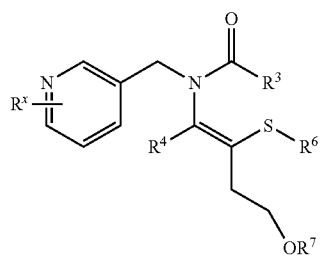

IIa

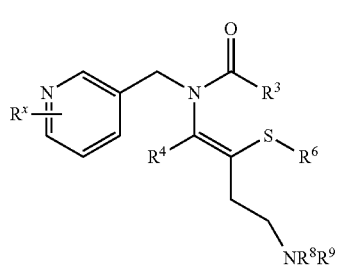

IIb

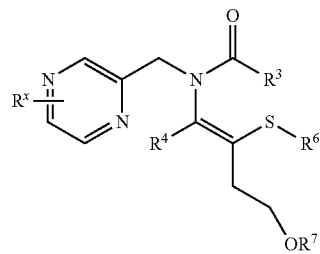

IIc

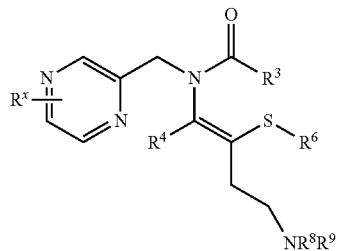

IId wherein R$^3$-R$^4$ and R$^6$-R$^9$ are as defined in formula I and R$^x$ denotes a suitable substituent of a heteroaryl ring as described above. Both the pyridyl and pyrazinyl rings may be substituted with one or more such R$^x$ groups (0-4 R$^x$ groups for pyridyl and 0-3 R$^x$ groups for pyrazinyl). In certain embodiments, R$^6$ is Y wherein R$^1$, R$^2$, ring A, R$^a$, R$^b$, R$^c$, R$^d$, n, and R$^5$ are as defined in formulae IIa, IIb, IIc and IId.

Preferred R$^x$ groups include, but are not limited to, —OC(O)R†, halo, —OR†, —CF$_3$, —OCF$_3$, —SCF$_3$, —SR†, —R†, —NR†C(O)R†, —CO$_2$R†, —NO$_2$, —N(R†)$_2$, —CN, —C(O)R†, —C(O)N(R†)$_2$, —SO$_2$N(R†)$_2$, —NR†CO$_2$R†, —C(O)C(O)R†, —OC(O)N(R†)$_2$, —S(O)$_t$R†, —C(O)CH$_2$C(O)R†, —NR+SO$_2$R†, and —C(=S)N(R†)$_2$, wherein the two R†s on the same nitrogen optionally taken together forming a 5-8 membered saturated, partially saturated or aromatic ring having additional 0-4 ring heteroatoms selected from oxygen, nitrogen and sulfur.

More preferred R$^x$ groups include, but are not limited to, —OC(O)R†, halo, —OR†, —CF$_3$, —OCF$_3$, —SCF$_3$, —SR†, R†, —NR†C(O)R†, —CO$_2$R†, —NO$_2$, —N(R†)$_2$, and —CN. In some embodiments, R† is 3-6 membered unsubstituted cycloalkyl, phenyl, benzyl, naphthyl, pyridyl, or C$_{1-6}$ alkyl optionally substituted with halo.

Preferred A rings are selected from the following:

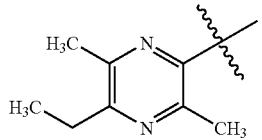

1

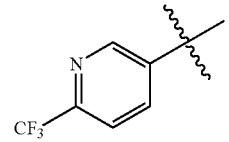

2

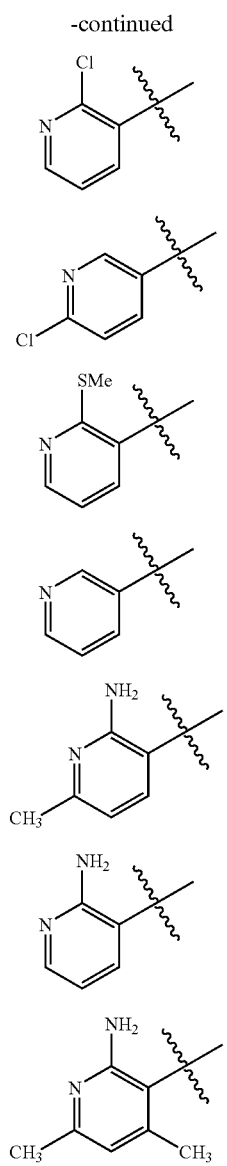

According to some embodiments of the present invention, n is 1.

In other embodiments, $R^1$, $R^2$ and $R^4$ are independently H, $C_{1-6}$ alkyl or fluoro($C_{1-6}$ alkyl). Examples of $R^1$, $R^2$ and $R^4$ include H, methyl, ethyl, —CH$_2$F, —CHF$_2$, —CF$_3$ and the like.

In some embodiments, $R^3$ is H, alkyl, fluoroalkyl, —(CH$_2$)$_{1-6}$OR, —(CH$_2$)$_{1-6}$N(R)$_2$, —NR°C(O)R, —C(O)R, —C(H)(OR)R, aralkyl, heterocyclyl, heterocyclylalkyl, heteroaryl, or heteroaralkyl. In other embodiments, $R^3$ is H, $C_{1-6}$ alkyl, —(CH$_2$)$_{1-6}$OR° or —CH(OR°)R°. Examples of $R^3$ include H, methyl, ethyl, —CH(OH)CH$_3$, —CH$_2$OH, —CH$_2$CH$_2$OH and the like.

In some embodiments, $R^6$ is —C=C—C(O)R, —SR, —S—W—OR$^7$, M or Y. In other embodiments, $R^6$ is —C=C—C(O)R, —SR, —S—W—OR$^7$ or Y. In other embodiments, $R^6$ is —S-(unsubstituted $C_{1-6}$ alkyl) or Y.

In some embodiments, W is alkylene. Examples of W include —CH$_2$—, —CH$_2$CH$_2$—, —CH$_2$CH$_2$CH$_2$— and the like.

In other embodiments, $R^6$ is —C=C—C(O)R, an alpha-, beta-unsaturated carbonyl moiety comprising a double bond having an alpha end and a beta end, the beta ending being accessible to glutathione in an addition-elimination reaction, wherein the resulting compound of formula I lacks an ionizable carboxylic acid group (see United States patent application US 2004/0023994 A1, content of which is incorporated herein by reference). Examples of such $R^6$ moieties include, but are not limited to, the following:

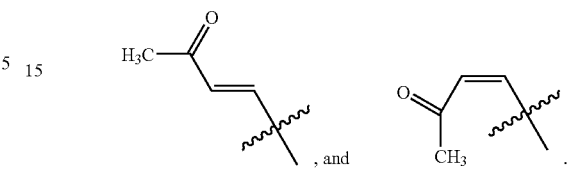

Without being bound by theory, compounds of formula I wherein the sulfur heteroatom is conjugated to an alpha-, beta-unsaturated carbonyl are metabolized more rapidly or in greater quantities than compounds not so conjugated in tumor cells which exhibit abnormal thiol metabolism and have increased levels of glutathione.

In some embodiments, $R^7$ is H, alkyl, —C(O)R, —PO$_3$M$_x$, —(PO$_3$)$_2$M$_y$, —P(O)(alkyl)OM', —C(O)N(R)$_2$, or —C(O)OR. In some embodiments, R is alkyl or aryl. Examples of $R^7$ include H, methyl, ethyl, —C(O)alkyl, —C(O)NMe$_2$, —C(O)-p-OMe-phenyl, —C(O)O-phenyl, —PO$_3$H$_2$, —P(O)(OMe)$_2$, —P(O)(OMe)OH, —P(O)(Me)OH, and —P(O)(OH)OP(O)(OH)(OH).

In some embodiments, $R^8$ is H or $C_{1-6}$ unsubstituted alkyl. Examples of $R^8$ include H, methyl, ethyl and the like.

In some embodiments, $R^9$ is H, alkyl, —C(O)R, —C(O)N(R)$_2$, —C(O)OR, —SO$_2$R, 5-membered heterocyclyl, or 5-membered heteroaralkyl. Examples of $R^9$ include H, methyl, ethyl, and the following:

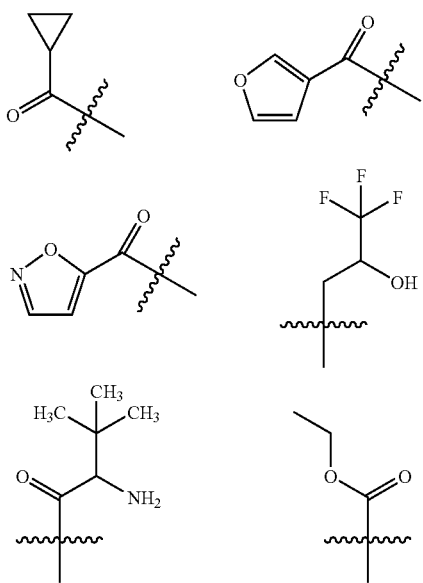

-continued

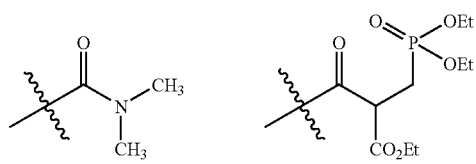
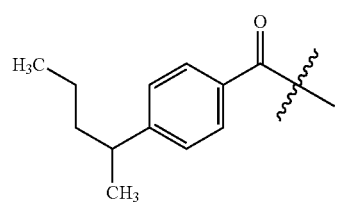
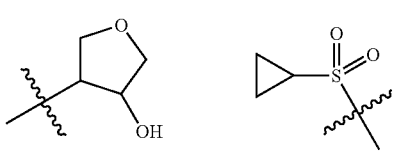
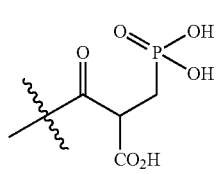
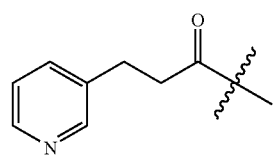
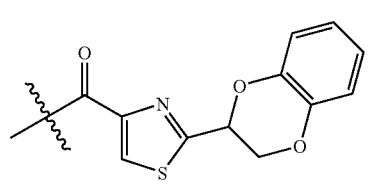
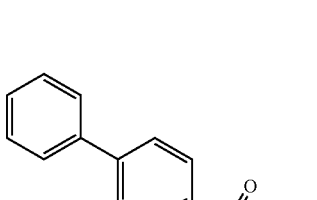
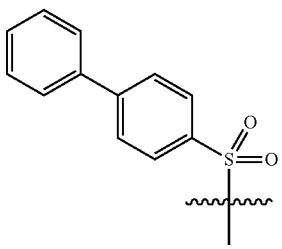
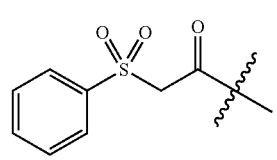

-continued

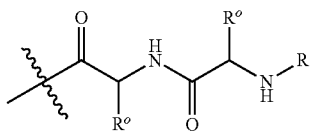

In other embodiments, $R^7$ or $R^9$ is a moiety that specifically targets tumor cells. Such $R^7$ or $R^9$ includes polysaccharides (e.g., hyaluronic acid (HA) and hyaluronic acid derivatives), oligopeptide analogs ($-[C(O)CH(R)N(R)]_{2-3}-R$; for example, compounds of formula 1 and 2) and antibodies.

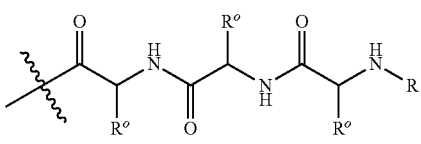

Examples of such tumor-targeting moieties are known in the art and include the following:

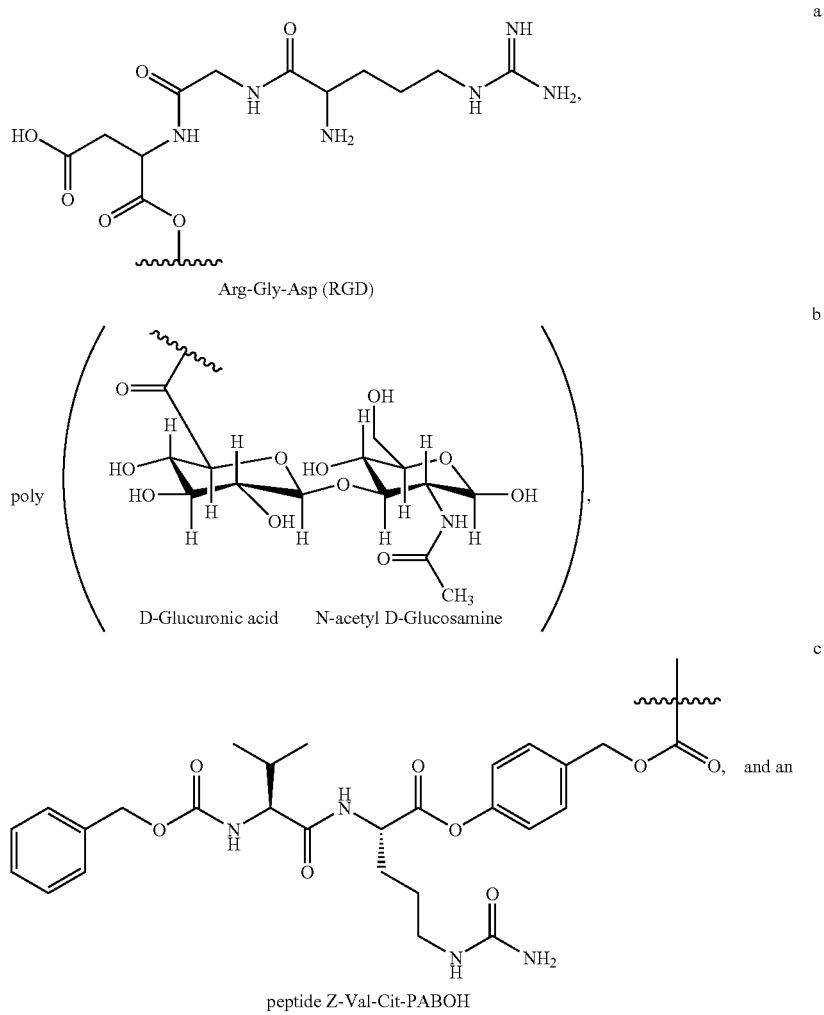

Arg-Gly-Asp (RGD)

poly( D-Glucuronic acid — N-acetyl D-Glucosamine ), peptide Z-Val-Cit-PABOH antibody.

Compounds with $R^7$ or $R^9$ tumor-targeting moieties can be prepared using methods known in the art. See, Luo et al., *Bioconjugate Chem.*, 1999, 10, 755-763; Janssen et al., *Cancer Research*, 2002, 62, 6146-6151; Curnis et al., *Cancer Research*, 2004, 64, 565-571; and Toki et al., *J. Org. Chem.* 2002, 67, 1866-1872. The resulting conjugate aids the delivery of the compounds of the present invention to a mammal. Preferably, the conjugate aids in delivering active compounds to one or more selective cell types, tissues or organs of the mammal, for example, by means of a cellular targeting molecule, e.g., an immunoconjugate or other cell surface specific conjugate. Useful tissues and organs include lymphatic tissue, blood, brain, kidney, liver, lung, spleen. Useful tissues are not, however, limited to these organs. Compounds of the present invention are envisioned to be effective for reducing tumor growth in any tumor type in the body.

For example, the Arg-Gly-Asp moiety (a) interacts with the cell adhesion receptors including $\alpha_v\beta_3$ which is selectively expressed in tumor cells. Therefore, RGD esters would deliver the active drug to the site of action.

Polysaccharide bioconjugate b (e.g., hyaluronic acid (HA) and hyaluronic acid derivatives) targets tumor cells expressing the HA receptor.

The peptide Z-Val-Cit-PABOH moiety (c) is cleaved by Cathepsin B in tumor cells to give the active drug. Proteolytic enzymes such as cathepsin B are often overexpressed by metastatic tumor cells. Cathepsin B, among others, has been recognized to be critical for the metastatic process because of its capability to degrade the basement membrane and the extracellular matrix around tumor tissue. Cathepsin B has been shown to be clinically relevant in cancer progression and its cytosolic levels can be up to 11 times higher in tumor tissue compared to normal tissue. This specific target delivery approach using the peptide Z-Val-Cit-PABOH favors intratumoral drug efficiency while minimizing non-targeted tissues.

In other embodiments the tumor-targeting moiety is an antibody. The antibody is raised against certain antigens expressed selectively or overexpressed on tumor cells. Such antibodies target the compounds of this invention to the tumor cells. Antibodies conjugated to a compound according to this invention are immunoglobulin molecules or portions thereof that are immunologically reactive with the antigens expressed on tumor cells.

Antibodies exist for example, as intact immunoglobulins (consisting of two heavy chains and two light chains) or as a number of well-characterized fragments thereof. Such fragments include, but are not limited to, those produced by digestion with various proteases, those produced by chemical cleavage and/or chemical dissociation, and those produced recombinantly, so long as the fragment remains capable of specific binding to an antigen. Among these fragments are Fab, Fab', F(ab')$_2$, and single chain Fv (scFv) fragments. Thus, as used herein, the term antibody includes antibody fragments produced by the modification of whole antibodies or those synthesized de novo.

In other embodiments the antibody is conjugated to a liposome comprising the compounds of this invention.

The invention also provides compounds of formula I wherein $R^7$ or $R^9$ is formula d:

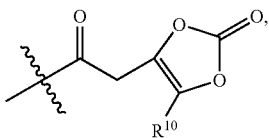

wherein $R^{10}$ is H, optionally substituted alkyl, or optionally substituted aryl (see Sun et al., *J. Med. Chem.*, 2001, 44, 2671-2674; Sun et al., *Tetrahedron Letters*, 2002, 43, 1161-1164; and U.S. Pat. No. 5,466,811, content of which is incorporated herein by reference).

The oxodioxolenylmethyl carbonate (d) conjugated prodrugs are characterized as being more readily bioavailable, less irritating to topical and gastric mucosal membranes and more permeable through topical membranes than are the parent drugs from which they are derived. Therefore, the oxodioxolenylmethyl carbonate (d) conjugated prodrugs provide increased biomembrane transport such that the drug is more bioavailable, for example, from the GI tract, the rectum, the skin and the eye.

Some embodiments of formula I have one or more, and more preferably all, of the features selected from the group consisting of:

i) $R^1$, $R^2$ and $R^4$ are independently H, $C_{1-6}$ alkyl or fluoro ($C_{1-6}$ alkyl);

ii) $R^3$ is H, alkyl, fluoroalkyl, —(CH$_2$)$_{1-6}$OR, —(CH$_2$)$_{1-6}$N(R)$_2$, —NR$^o$C(O)R, —C(O)R, —C(H)(OR)R, aralkyl, heterocyclyl, heterocyclylalkyl, heteroaryl, or heteroaralkyl;

iii) $R^6$ is —C≡C—C(O)R, —SR, —S—W—OR$^7$, M or Y;

iv) $R^7$ is H, alkyl, —C(O)R, —PO$_3$M$_x$, —(PO$_3$)$_2$M$_y$, —P(O)(alkyl)OM', —C(O)N(R)$_2$, —C(O)OR, or a tumor-targeting moiety; or $R^9$ is H, alkyl, —C(O)R, —C(O)N(R)$_2$, —C(O)OR, —SO$_2$R, 5-membered heterocyclyl, 5-membered heteroaralkyl, or a tumor-targeting moiety; and v) n is 1.

In some embodiments, R is R$^o$, carbocyclyl, aryl, heteroaryl, heterocyclyl, aralkyl, heterocyclylalkyl, or heteroaralkyl. In other embodiments, R$^o$ is H or $C_{1-6}$ alkyl optionally substituted with halo, hydroxy or amino.

Other embodiments of the present invention have one or more, and more preferably all, of the features selected from the group consisting of:

i) ring A is optionally substituted with —OC(O)R$^†$, halo, —OR$^†$, —CF$_3$, —OCF$_3$, —SCF$_3$, —SR$^†$, —R$^†$, —NR$^†$C(O)R$^†$, —CO$_2$R$^†$, —NO$_2$, —N(R$^†$)$_2$, —CN, —C(O)R$^†$, —C(O)N(R$^†$)$_2$, —SO$_2$N(R$^†$)$_2$, —NR$^†$CO$_2$R$^†$, —C(O)C(O)R$^†$, —OC(O)N(R$^†$)$_2$, —S(O)$_r$R$^†$, —C(O)CH$_2$C(O)R$^†$, —NR$^+$SO$_2$R$^†$, or —C(=S)N(R$^†$)$_2$; and R$^†$ is 3-6 membered unsubstituted cycloalkyl, phenyl, benzyl, naphthyl, pyridyl, or $C_{1-6}$ alkyl optionally substituted with halo;

ii) $R^3$ is H, $C_{1-6}$ alkyl, —(CH$_2$)$_{1-6}$OR$^o$ or —CH(OR$^o$)R$^o$;

iii) $R^6$ is —C≡C—C(O)R, —SR, —S—W—OR$^7$ or Y;

iv) $R^8$ is H or $C_{1-6}$ unsubstituted alkyl; and v) n is 1.

Some embodiments of the present invention have one or more, and more preferably all, of the features selected from the group consisting of:

i) ring A is optionally substituted with —OC(O)R$^†$, halo, —OR$^†$, —CF$_3$, —OCF$_3$, —SCF$_3$, —SR$^†$, —R$^†$, —NR$^†$C(O)R$^†$, —CO$_2$R$^†$, —NO$_2$, —N(R$^†$)$_2$, —CN, —C(O)R$^†$, —C(O)N(R$^†$)$_2$, —SO$_2$N(R$^†$)$_2$, —NR$^†$CO$_2$R$^†$, —C(O)C(O)R$^†$, —OC(O)N(R$^†$)$_2$, —S(O)$_r$R$^†$, —C(O)CH$_2$C(O)R$^†$, —NR$^+$SO$_2$R$^†$, or —C(=S)N(R$^†$)$_2$; and R$^†$ is 3-6 membered unsubstituted cycloalkyl, phenyl, benzyl, naphthyl, pyridyl, or $C_{1-6}$ alkyl optionally substituted with halo;

ii) $R^3$ is H, $C_{1-6}$ alkyl, —(CH$_2$)$_{1-6}$OR$^o$ or —CH(OR$^o$)R$^o$;

iii) $R^6$ is —C≡C—C(O)R, —SR, —S—W—OR$^7$ or Y;

iv) $R^8$ is H or $C_{1-6}$ unsubstituted alkyl;

v) $R^7$ or $R^9$ is a polysaccharide, —[C(O)CH(R)N(R)]$_{2-3}$—R, an antibody, or

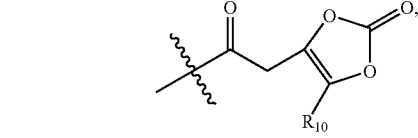

wherein $R_{10}$ is H, alkyl, or aryl; and vi) n is 1.

Other embodiments of the present invention have one or more, and more preferably all, of the features selected from the group consisting of:

i) ring A is selected from the group consisting of 1-9;

ii) $R^1$, $R^2$ and $R^4$ are independently H, methyl, ethyl, —CH$_2$F, —CHF$_2$, or —CF$_3$;

iii) $R^3$ is H, methyl, ethyl, —CH(OH)CH$_3$, —CH$_2$OH, or —CH$_2$CH$_2$OH;

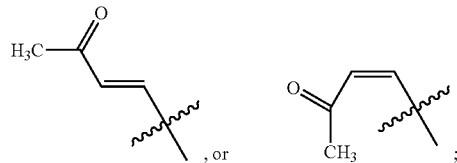

iv) $R^6$ is —S-(unsubstituted $C_{1-6}$ alkyl), Y, v) $R^8$ is H, methyl, or ethyl; and vi) $R^7$ is H, methyl, ethyl, —C(O)Me, —C(O)Et, —C(O)NMe$_2$, —C(O)-p-OMe-phenyl, —C(O)O-phenyl, —PO$_3$H$_2$, —P(O)(OMe)$_2$, —P(O)(OMe)OH, —P(O)(Me)OH, —P(O)(OH)OP(O)(OH)(OH), or $R^{11}$; and $R^{11}$ is selected from the group consisting of:

a
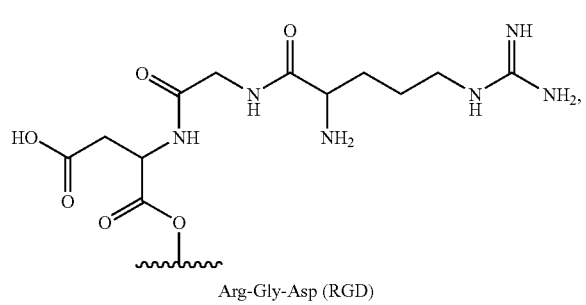
Arg-Gly-Asp (RGD)
b
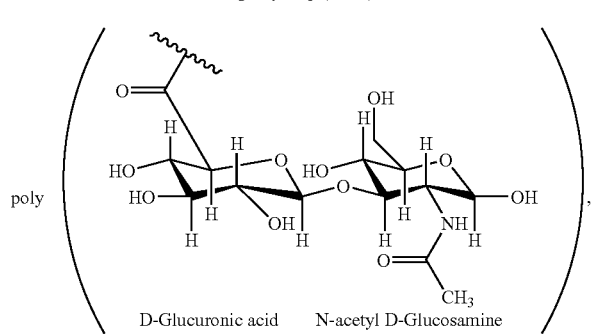
c
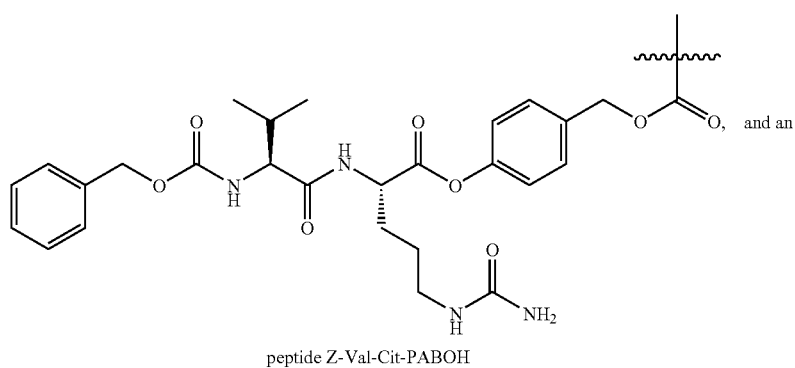
peptide Z-Val-Cit-PABOH
and an antibody; or $R^9$ is H, methyl, ethyl, $R^{11}$,
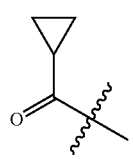 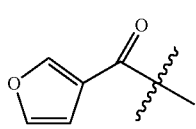
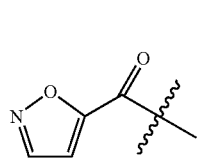 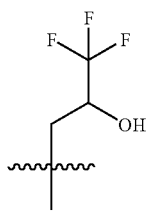
-continued
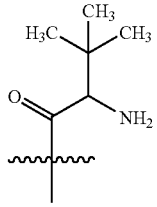 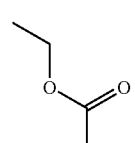
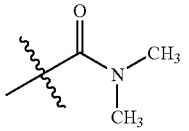 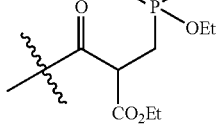
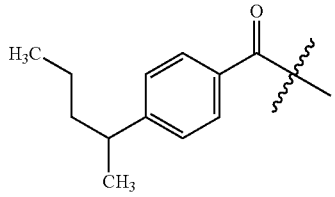

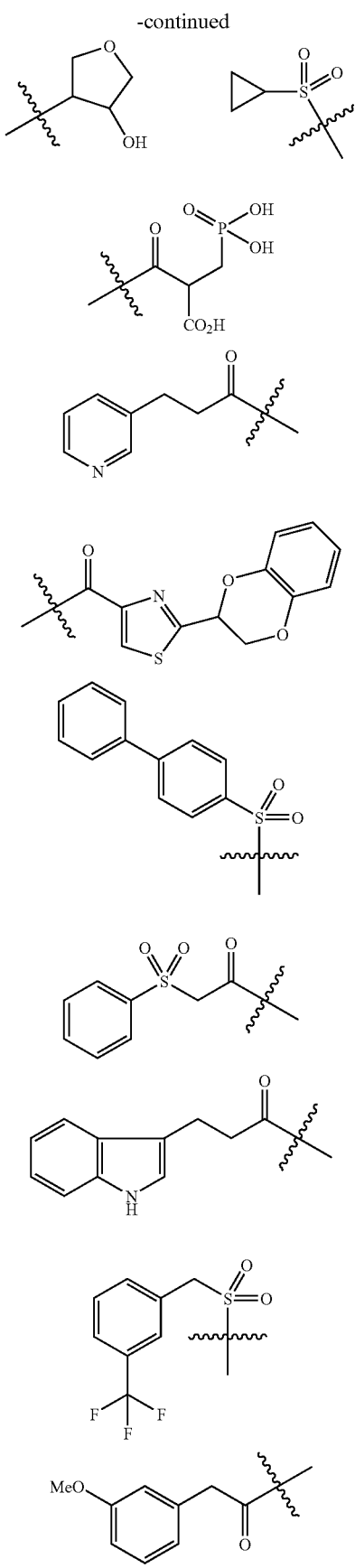
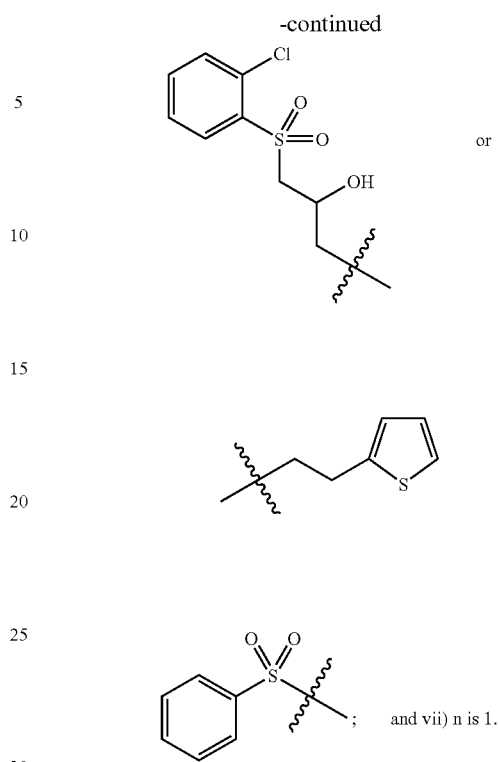
; and vii) n is 1.
Representative compounds of formula I are depicted in Tables 1 and 2 below (the fragment numbers refer to the structures illustrated for ring A shown above).
TABLE 1
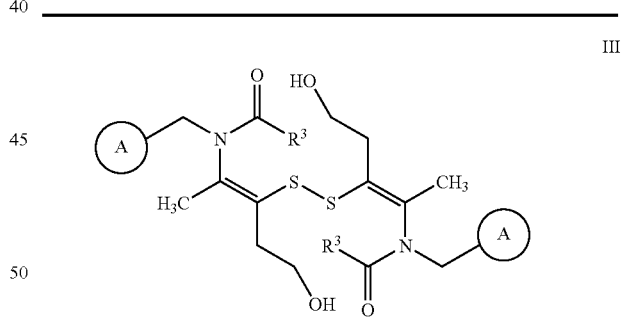
| Cpd. No. | Ring A | R³ | Cpd. No. | Ring A | R³ |
|---|---|---|---|---|---|
| III-1 | 1 | H | III-2 | 1 | CH₃ |
| III-3 | 2 | H | III-4 | 2 | CH₃ |
| III-5 | 3 | H | III-6 | 3 | CH₃ |
| III-7 | 4 | H | III-8 | 4 | CH₃ |
| III-9 | 5 | H | III-10 | 5 | CH₃ |
| III-11 | 6 | H | III-12 | 6 | CH₃ |
| III-13 | 7 | H | III-14 | 7 | CH₃ |
| III-15 | 8 | H | III-16 | 8 | CH₃ |
| III-17 | 9 | H | III-18 | 9 | CH₃ |

TABLE 2

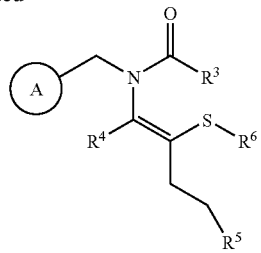

IV

| Cpd. No. | Ring A | R³ | Cpd. No. | Ring A | R³ |
|---|---|---|---|---|---|
| IV-1 | 1 | H | IV-2 | 1 | CH₃ |
| IV-3 | 2 | H | IV-4 | 2 | CH₃ |
| IV-5 | 3 | H | IV-6 | 3 | CH₃ |
| IV-7 | 4 | H | IV-8 | 4 | CH₃ |
| IV-9 | 5 | H | IV-10 | 5 | CH₃ |
| IV-11 | 6 | H | IV-12 | 6 | CH₃ |
| IV-13 | 7 | H | IV-14 | 7 | CH₃ |
| IV-15 | 8 | H | IV-16 | 8 | CH₃ |
| IV-17 | 9 | H | IV-18 | 9 | CH₃ |

The compounds of this invention generally may be obtained from known or readily prepared starting materials, following methods known to those skilled in the art, such as that illustrated by general Scheme I below, wherein R³-R⁶ and ring A are as defined in formula I, and by the examples described herein.

Scheme I

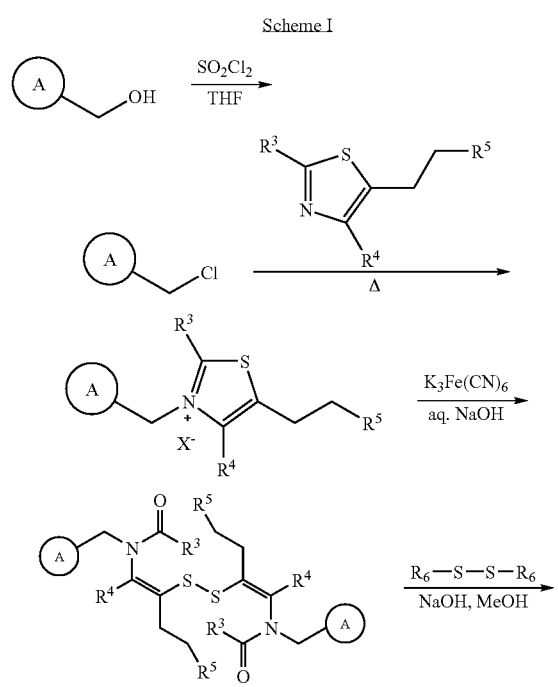

$X^-$ is a suitable counterion, such as $Cl^-$, $Br^-$, $F^-$, $I^-$, $NO_3^-$, acetate, trifluoroacetate, benzoate, maleate, and methanesulfonate.

Compounds with $R^1$, $R^2$, n, and $R^a$-$R^d$ other than those illustrated in Scheme I may be synthesized by modifying the synthetic routes disclosed herein using methods known in the art.

Compounds of the present invention are useful as transketolase inhibitors. One aspect of the instant invention relates to methods of inhibiting transketolase activity in a biological sample comprising contacting the biological sample with compounds of formula I or pharmaceutically acceptable derivatives thereof. Another aspect of the instant invention relates to methods of inhibiting transketolase activity in a patient comprising administering to the patient in need thereof with a therapeutically effective amount of compounds of formula I or pharmaceutically acceptable derivatives thereof. The inhibitory activity of the present compounds towards transketolase may be assayed by methods known in the art (see, for example, Booth and Nixon, *Eur. J Biochem.* 1993, 218:261-265). In a preferred embodiment, the present compounds selectively inhibit transketolase activity compared to their ability to inhibit another TPP-utilizing enzyme (e.g., alpha-ketoglutarate dehydrogenase or pyruvate dehydrogenase).

The amount of the present compounds needed to achieve a therapeutic effect will vary depending on the individual tumor and subject treated, and may be determined empirically by one of skill in the art, e.g., by measuring transketolase activity in a tumor biopsy or in the blood of the treated subjects. In general, the level will depend on competing levels of thiamine and thiamine-derived compounds such as thiamine pyrophosphate (TPP), which is the cofactor for transketolase. The recommended daily allotment (RDA) of thiamine in humans is 1.5 mg. For a human weighing 70 kg, that corresponds to a recommended daily intake of 21 micrograms/kg body weight. The average 20 g mouse which ingests 1 g of food per day (mouse chow, Taklad Global 18%, contains 10 mg thiamine/kg), has a daily intake of about 500 micrograms/kg body weight. The skilled artisan may determine empirically a therapeutically effective range of the present compounds by taking into consideration estimated or measured thiamine levels in the subject to be treated.

According to one embodiment of the invention, compounds of formulae I, IIa-d, III or IV or derivatives thereof may be formulated into compositions. In one embodiment, the composition is a pharmaceutical composition, which comprises a compound of formulae I, IIa-d, III or IV or derivatives thereof and pharmaceutically acceptable carrier, adjuvant or vehicle. In another embodiment, the composition comprises an amount of a transketolase inhibitor of the present invention effective to inhibit transketolase activity in a biological sample or in a patient. In another embodiment, compounds of this invention and pharmaceutical compositions thereof may be formulated for administration to a patient, for example, for oral administration, to treat or prevent cancer.

The term "pharmaceutically effective amount" or "therapeutically effective amount" refers to an amount of a compound of this invention that is effective in treating cancer, in a patient either as monotherapy or in combination with other agents.

The amount effective to inhibit transketolase activity is one that measurably inhibits the transketolase activity when compared to the activity of the enzyme in the absence of an inhibitor. Measurable inhibition means a measurable change in activity between a sample containing said inhibitor and transketolase and a sample containing said transketolase.

Treatment of cancer includes any medical intervention resulting in the slowing of tumour growth or reduction in tumour metastases, as well as partial remission of the cancer in order to prolong life expectancy of a patient. As used herein, the term "patient" refers to a mammal, including a human.

As used herein, the term "subject" refers to a patient or a biological sample. The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof. The term "tumor-derived cell" refers to a cell extracted from a tumor in a subject that has been cultured separately from the tumor, in vitro or in vivo.

The term "pharmaceutically acceptable carrier, adjuvant or vehicle" refers to a carrier, adjuvant or vehicle that may be administered to a patient, together with a compound of this invention, and which does not destroy the pharmacological activity thereof and is nontoxic when administered in doses sufficient to deliver a therapeutic amount of the therapeutic agent.

The term "pharmaceutically acceptable derivative" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives are those that increase the bioavailability of the compounds of this invention when such compounds are administered to a patient (e.g., by allowing an orally administered compound to be more readily absorbed into the blood) or which enhance delivery of the parent compound to a biological compartment relative to the parent species.

Throughout this specification, the word "comprise" or variations such as "comprises" or "comprising" will be understood to imply the inclusion of a stated integer or groups of integers but not the exclusion of any other integer or group of integers.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium, $NW_4^+$ (wherein W is $C_{1-4}$ alkyl) and other amine salts. Physiologically acceptable salts of a hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$alkyl group).

Any reference to any of the above compounds also includes a reference to a pharmaceutically acceptable derivative thereof, such as a pharmaceutically acceptable salt, ester, and salt of an ester.

Salts of the compounds of the present invention may be made by methods known to a person skilled in the art. For example, treatment of a compound of the present invention with an appropriate base or acid in an appropriate solvent will yield the corresponding salt.

Esters of the compounds of the present invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

In such esters, unless otherwise specified, any alkyl moiety present preferably contains from 1 to 18 carbon atoms, particularly from 1 to 6 carbon atoms, more particularly from 1 to 4 carbon atoms, Any cycloalkyl moiety present in such esters preferably contains from 3 to 6 carbon atoms. Any aryl moiety present in such esters preferably comprises a phenyl group.

The present invention provides compounds and pharmaceutical compositions thereof and methods of using them to treat (i.e., ameliorate, mitigate, alleviate, slow, or inhibit) or prevent hyperproliferative diseases, such as cancers including but not limited to breast, prostate, ovarian, stomach, colerectal, skin, lung, cervical and bladder cancers, glioma, mesothelioma, as well as various leukemias and sarcomas, such as Kaposi's Sarcoma. The present compounds and pharmaceutical compositions are also useful to inhibit tumor growth, angiogenesis, metastasis and/or otherwise inappropriate cell proliferation. While not intending to be bound by theory, the present compounds inhibit tumor growth by inhibiting non-oxidative pentose phosphate pathways in cells and tumors. The invention thus provides additional methods for using the present compounds and compositions thereof, based on the biochemical activity of the present compounds in a cell.

Transketolase is known to participate in the non-oxidative pentose phosphate pathway which stimulates ribose biosynthetic pathways and thus increases steady-state levels of ribulose-5 phosphate and ribose-5-phosphate in a cell. In another embodiment, the invention provides a method for reducing levels of ribulose-5-phosphate or ribose-5-phosphate in a tumor cell comprising administering to the cell an effective amount of a present compound.

Moreover, steady-state levels of pentose phosphates, such as ribulose-5-phosphate and ribose-5-phosphate (a substrate for nucleic acid synthesis), influence nucleic acid biosynthetic rates. Thus, in another embodiment, the invention provides a method for inhibiting nucleic acid synthesis in a tumor cell comprising administering to the cell an effective amount of a present compound.

Increased nucleic acid biosynthesis is required for cell proliferation. Thus in another embodiment, the invention provides a method for inhibiting cell proliferation of a tumor or tumor-derived cell comprising administering to the cell an effective amount of a present compound.

According to some embodiments, the invention provides an inhibitor that inhibits the proliferation of tumor cells in vivo. The tumor cell may be derived from any cell type including, without limitation, epidermal, epithelial, endothelial or mesodermal cells. The tumor cells may be derived from solid or non-solid tumors including, but not limited to, leukemia, sarcoma, multiple myeloma, glioblastoma, choriocarcinoma, Kaposi or cervical intraepithelial neoplasia. In another embodiment, an inhibitor of the present invention inhibits prostate, colon, breast, sarcoma, ovarian, lung and glioblastoma tumor growth in a subject.

In another embodiment, the invention provides a method for stimulating apoptosis in a tumor or tumor-derived cell comprising administering to the cell an effective amount of a present compound.

In another embodiment, the invention provides a method for reducing tumor growth, thus treating cancer, in a patient comprising administering an effective amount of a present compound to the patient in need thereof.

In some embodiments, an inhibitor of the invention is used to treat lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

In yet a further aspect, the present invention provides the use of a compound according to the invention in the manufacture of a medicament for the treatment or prophylaxis of cancer and associated conditions.

The above compounds according to the invention and their pharmaceutically acceptable derivatives may be employed in combination with other therapeutic agents for the treatment of the above conditions. Combination therapies according to the present invention comprise the administration of a compound of the present invention or a pharmaceutically acceptable derivative thereof and another pharmaceutically active agent. The active ingredient(s) and pharmaceutically active agents may be administered simultaneously (i.e., concurrently) in either the same or different pharmaceutical compositions or sequentially in any order. The amounts of the active ingredient(s) and pharmaceutically active agent(s) and the relative timings of administration will be selected in order to achieve the desired combined therapeutic effect.

Such therapeutic agents may also be a chemotherapeutic agent, an antiangiogenic agent, an agent which modulates signaling associated with hypoxic conditions in a cell (e.g., Avastin™ (bevacizumab), angiostatin and endostatin). Other therapeutic agents that may be used in combination with the present compounds or compositions include, but are not limited to, cancer therapeutics such as mitotic inhibitors, alkylating agents, alpha-metabolites, intercalating antibiotics, growth factor inhibitors, cell cycle inhibitors, enzymes, topoisomerase inhibitors, anti-metastatic agents, anti-angiogenic agents and radiation. Exemplary cancer therapeutics are farnesyl transferase inhibitors, tamoxifen, herceptin, taxol, ST1571, cisplatin, 5-flurouracil and cytoxan, some of which specifically target members of the ras tumorigenic pathway.

The present compounds and compositions can also be used in combination with agents that create a hypoxic environment. Hypoxia, i.e., lack of oxygen, plays a fundamental role in many pathologic processes. In response to hypoxia, cells activate and express multiple genes. Tumor cells may respond to hypoxia by diminishing their proliferative rates leaving the cells viable but nonproliferating. Some transformed cell lines can also undergo apoptosis in extreme hypoxia and an acidic environment.

Further, without being limited to any particular mechanism of action, the tumor inhibiting effect of the present compounds or compositions may be associated with inhibition of the non-oxidative pentose phosphate pathway which shuttles carbon from glycolytic reactions to the formation of pentose phosphates used in nucleic acid biosynthesis, including ribulose-5-phosphate and ribose-5-phosphate. Accordingly, in some embodiments, one or more hypoxia-inducing agents are administered simultaneously with, prior to, or subsequent to administration of the present compounds or compositions. The hypoxia-inducing agent may be administered in the same composition comprising the present compounds or may be administered in a separate composition.

When the present compounds and compositions are used to inhibit tumor cell growth, various stages of cancer are treated by these methods, including neoplasia and malignant tumors. Cancers that can be treated by these methods include, without limitation, cancers that have failed other therapies, cancers at various stages of evolution (including recurring, resistant and minimal residual cancers), cancers whose etiology involves ras, myc, p53, and all other oncogenes whose expression or mis-expression affects signal transduction pathways involved in cell growth, division, proliferation, apoptosis and/or cell death.

The present invention further includes the use of a compound according to the invention in the manufacture of a medicament for simultaneous or sequential administration with at least another therapeutic agent, such as those defined hereinbefore.

In general a suitable dose for each of the above-mentioned conditions will be in the range of 0.01 to 600 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. Unless otherwise indicated, all weights of active ingredient are calculated as the parent compound of formula I; for derivatives, such as salts and esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, preferably 20 to 500 mg, and most preferably 50 to 400 mg of active ingredient per unit dosage form.

While it is possible for the active ingredient to be administered alone, it is preferable to present it as a pharmaceutical composition. The compositions of the present invention comprise at least one active ingredient, as defined above, together with one or more acceptable carriers thereof and optionally other therapeutic agents. Each carrier must be acceptable in the sense of being compatible with the other ingredients of the composition and not injurious to the patient.

Pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable derivative thereof and another therapeutic agent are presented separately from one another as a kit of parts. The present compositions can also be used in combination with other cancer therapies involving, e.g., radiation, photosensitizing compounds, anti-neoplastic agents and immunotoxics.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3(6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray Pharmaceutical compositions containing in addition to the active ingredient such carriers as are known in the art to be appropriate.

Pharmaceutical compositions for rectal administration may be presented as a suppository with a suitable carrier comprising, for example, cocoa butter or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

In certain preferred embodiment, each of the above-described methods is performed on a cell or cells in which the thiamine concentration has been reduced, as described below.

A typical Western diet is rich in thiamine and many cancer patients take vitamin supplements containing thiamine. Without being bound by theory, some of the present compounds are competitive inhibitors of transketolase. Thus, the present compounds will be more effective as an anti-cancer agent when combined with a low-thiamine diet, wherein vitamin supplements that contain thiamine and thiamine-supplemented or thiamine-rich foods are avoided. Any other method for reducing cellular concentrations of thiamine are envisioned to be useful in combination with the treatment methods of the invention.

Accordingly, the invention also provides therapeutic methods which comprise the step of administering a present compound or a pharmaceutical composition thereof to a subject in which the thiamine concentration in the subject has been reduced. Preferably, thiamine concentrations in the subject are limited during the administration step. More preferably, steps taken to limit thiamine concentrations in the subject are started before the administration of a present compound, e.g., at least 24 hours before, preferably at least 48 hours before, more preferably at least a week before, and most preferably at least two weeks before the administration step. In addition, it is preferred that thiamine levels continue to be controlled post administration, e.g., for at least 24 hours, preferably at least 48 hours, more preferably at least a week, and most preferably at least two weeks after the administration step. The recommended minimum thiamine intake level is one that is sufficient to avoid symptoms of toxicity associated with thiamine deficiency. Such symptoms, which are usually mild but can become severe in some instances, include (but are not limited to) those of the cardiovascular and nervous systems such as those associated with wet or dry beriberi or neuropathy and/or Wernicke-Korsakoff syndrome, including peripheral vasodilation, biventricular myocardial failure, sodium and water retention, edema, fulminant cardiovascular collapse, confusion, disordered ocular motility, ataxia of gait, neuropathy and cerebellar degeneration. See, e.g., Singleton and Martin, *Curr. Molecular Medicine* 1:197-207 (2001).

In order that the invention described herein be more fully understood, the following examples are set forth. It should be understood that these examples are for illustrative purposes only and are not to be construed as limiting this invention in any manner.

EXAMPLES

Example 1

N-(2-Amino-6-methylpyridin-3-ylmethyl)-N-{2-[2-[(2-amino-6-methyl-pyridin-3-ylmethyl)formylamino]-1-(2-hydroxyethyl)-propenyldisulfanyl]-4-hydroxy-1-methylbut-1-enyl}formamide (III-13)

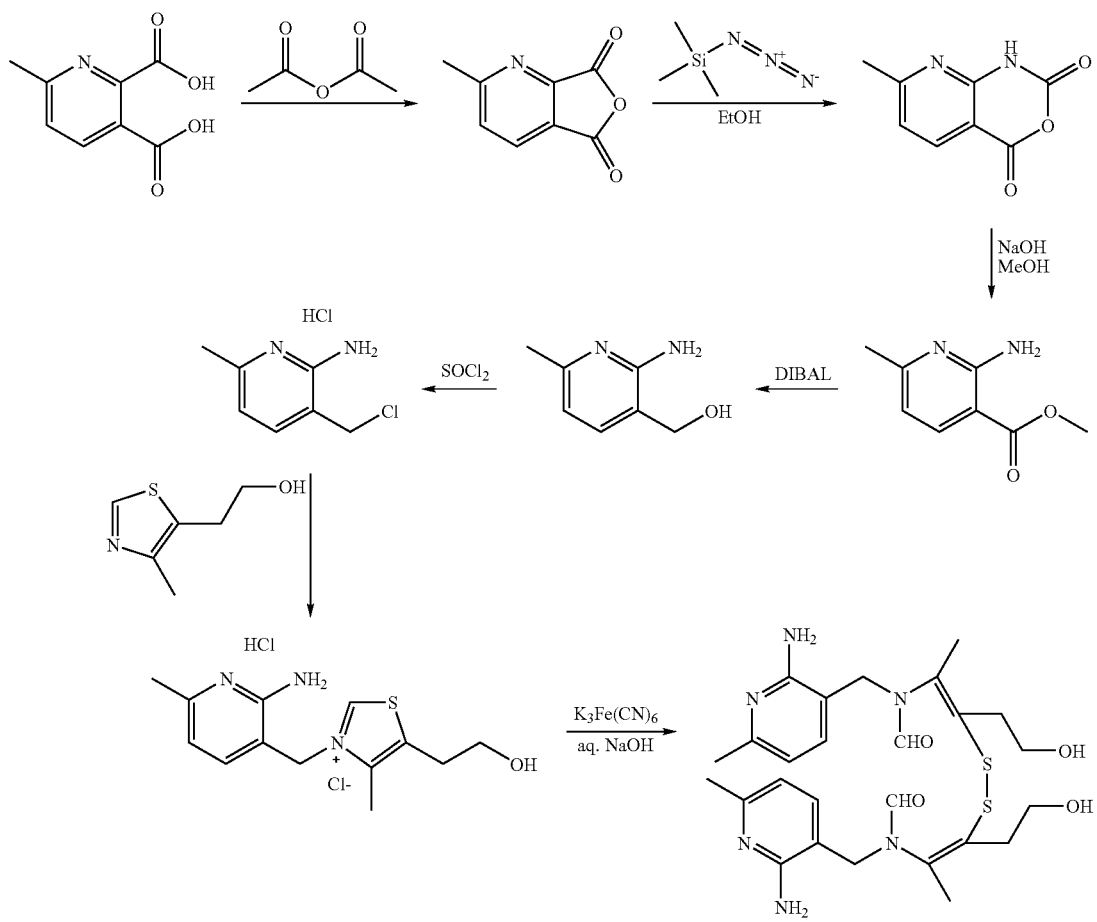

a) 2-Methylfuro[3,4-b]pyridine-5,7-dione. To a solution of 6-methyl-2,3-pyridinedicarboxylic acid (41.5 g, 229 mmol) and acetic anhydride (70 mL) in 250 mL of 1,2-dimethoxyethane was added pyridine (37 mL). The reaction mixture was stirred at room temperature for 90 min. The solution was diluted with ether (50 mL) and hexane (150 mL) was added until the solution became cloudy. The solution was stirred in an ice-water bath until a white precipitate formed. The precipitated solid was collected by filtration and dried under vacuum overnight to give 20.7 g (55%) of the title compound as a white crystalline solid. $^1$H NMR (CDCl$_3$) δ 2.85 (s, 3H), 7.68 (d, 1H), 8.25 (d, 1H).

b) 7-Methyl-1H-pyrido[2,3-d][1,3]oxazine-2,4-dione. To a solution of 2-methylfuro[3,4-b]pyridine-5,7-dione (20.0 g, 123 mmol) in chloroform (100 mL) was added azidotrimethylsilane (13.6 mL, 123 mmol). The resulting solution was stirred at room temperature for 50 min., then heated to reflux for one hour. The reaction mixture was cooled to room temperature and ethanol (7.2 mL) was added. A yellow precipitate formed and the suspension was placed in the freezer overnight. The precipitated solid was collected by filtration and washed with a generous portion of chloroform. The solid was dried to give 12.7 g of yellow powder. Analysis of this material showed it to be an approximate 3:1 mixture of the two possible regioisomers (total yield 58%). This crude material was carried on directly to the next reaction and the products separated at that time (see infra).

c) Methyl 2-amino-6-methylnicotinate. A solution of 7-methyl-1H-pyrido[2,3-d][1,3]oxazine-2,4-dione (12.5 g, mixture of isomers, 70.2 mmol) in a 0.1M solution of sodium hydroxide in methanol (702 mL, 70.2 mmol) was stirred and heated to 50° C. for 3 hours. The solvent was evaporated and the residual semi-solid was partitioned between ethyl acetate (800 mL) and 1.0M sodium hydroxide (800 mL). The organic layer was washed with brine, dried over sodium sulfate, and evaporated to give a pale-yellow solid. The isomers were separated by chromatography on silica gel (Biotage 75M column, eluent 25% hexanes in ethyl acetate, fraction size 500 mL). Fractions 7-12 were pooled and evaporated to give 7.3 g (62%) of the title compound as a white powder. MS(LC/MS/pos): 166.9 (M+H)$^+$. $^1$H NMR (CDCl$_3$) δ 2.40 (s, 3H), 3.85 (s, 3H), 6.47 (d+bs, 3H), 8.00 (d, 1H).

d) (2-Amino-6-methylpyridin-3-yl)methanol. To a 250 mL flask was added methyl 2-amino-6-methylnicotinate (0.85 g, 5.11 mmol) and toluene (5 mL). The reaction was cooled in an ice bath to 0° C. and diisobutylaluminum hydride (4.36 g, 30.7 mmol) was added dropwise and the reaction was warmed to room temperature over 1 hour. Saturated Rochelle's salt solution (5 mL) was added and the mixture was stirred for 2 hr. The resulting precipitate was removed by filtration. The filtrate was diluted with ethyl acetate (50 mL) and the organic layer was washed with brine. The organic layer was dried over sodium sulfate and concentrated to give a dark yellow oil. This material was further purified by chromatography on silica gel (Biotage 15, eluting with 20% 7N methanolic ammonia in dichloromethane) to give 0.50 g (71%) of the title compound as a clear oil. LCMS (APCI$^+$) R$_T$=1.42 min. m/z 139.0 (M+H). $^1$H NMR (400 MHz, CDCl$_3$) δ 7.16 (d, 1H, J=7.42 Hz, Ar—H), 6.42 (d, 1H, J=7.42 Hz, Ar—H), 5.01 (s, 2H, Ar—NH$_2$), 4.55 (s, 2H, Ar—CH$_2$OH), 2.30 (s, 3H, Ar—CH$_3$).

e) 3-Chloromethyl-6-methylpyridin-2-ylamine hydrochloride. To a 25 mL flask was added (2-amino-6-methylpyridin-3-yl)methanol (1.23 g, 8.90 mmol) and tetrahydrofuran (10 mL). Under vigorous stirring was added thionyl chloride (1.11 g, 9.35 mmol), dropwise over 5 min. The mixture was stirred for 30 min and concentrated to dryness to give 1.60 g (94%) of the title compound as a bright yellow solid. $^1$H NMR (400 MHz, CDCl$_3$) δ 7.75 (d, 1H, J=7.81 Hz, Ar—H), 7.56 (s, 2H, Ar—NH$_2$), 6.62 (d, 1H, J=7.81 Hz, Ar—H), 4.69 (s, 2H, Ar—CH$_2$OH), 2.61 (s, 3H, Ar—CH$_3$).

f) 3-(3-Amino-5-methylpyrazin-2-ylmethyl)-5-(2-hydroxyethyl)-4-methylthiazol-3-ium chloride hydrochloride. To a 20 mL flask was added 2-(4-methylthiazol-5-yl)ethanol (10.4 g, 72.5 mmol). The flask was placed in an oil bath heated to 100° C. 3-Chloromethyl-6-methylpyridin-2-ylamine hydrochloride (0.700 g, 3.63 mmol) was added as a solid in 0.1 g portions over 10 min and the reaction was stirred for 1 hr. The mixture was cooled to room temperature and the product was precipitated by addition of dichloromethane (100 mL). The product was collected by filtration and washed with dichloromethane (5×20 mL), then dried under vacuum, to give 0.75 g (62%) of the title compound as an off white powder. $^1$H NMR (400 MHz, D$_2$O) δ 9.43 (s, 1H, Ar—H), 7.45 (d, 1H, J=7.81 Hz, Ar—H), 6.68 (d, 1H, J=7.81 Hz, Ar—H), 5.41 (s, 2H, ArCH$_2$Ar), 3.71 (t, 2H, J=5.86 Hz, Ar—CH$_2$CH$_2$OH), 3.02 (t, 2H, J=5.86 Hz, Ar—CH$_2$CH$_2$OH), 2.37 (s, 3H, Ar—CH$_3$), 2.34 (s, 3H, Ar—CH$_3$).

g) N-(2-Amino-6-methylpyridin-3-ylmethyl)-N-{2-[2-[(2-amino-6-methyl-pyridin-3-ylmethyl)formylamino]-1-(2-hydroxyethyl)-propenyldisulfanyl]-4-hydroxy-1-methyl-but-1-enyl}formamide. 3-(2-Amino-6-methylpyridin-3-ylmethyl)-5-(2-hydroxyethyl)-4-methylthiazol-3-ium chloride hydrochloride (200 mg, 0.8 mmol) was dissolved in water (1 mL) and the pH of the solution was adjusted to 11-12 with 10% aqueous sodium hydroxide. A 20% solution of potassium ferricyanide (1 mL) was then added and the solution stirred for 1 minute at room temperature. The resulting yellow solution was extracted with a mixture of chloroform and isopropyl alcohol (3:1), and the combined organic phase was washed with brine and dried over magnesium sulfate. Evaporation of the solvent gave 176 mg (83%) of the title compound as a tan solid. $^1$H NMR (CDCl$_3$) δ 1.97 (s, 3H), 2.35 (s, 3H), 2.40 (bs, 2H), 3.50 (br. s, 2H), 5.35 (br. s, 2H), 6.37 (d, 1H), 7.00 (d, 1H), 7.90 (s, 1H); MS (APCI+) m/z (rel intensity) 561.1 (40), 280.1 (40).

Example 2

N-(2-Amino-6-methylpyridin-3-ylmethyl)-N-(4-hydroxy-1-methyl-2-propyldisulfanylbut-1-enyl)formamide (IV-13)

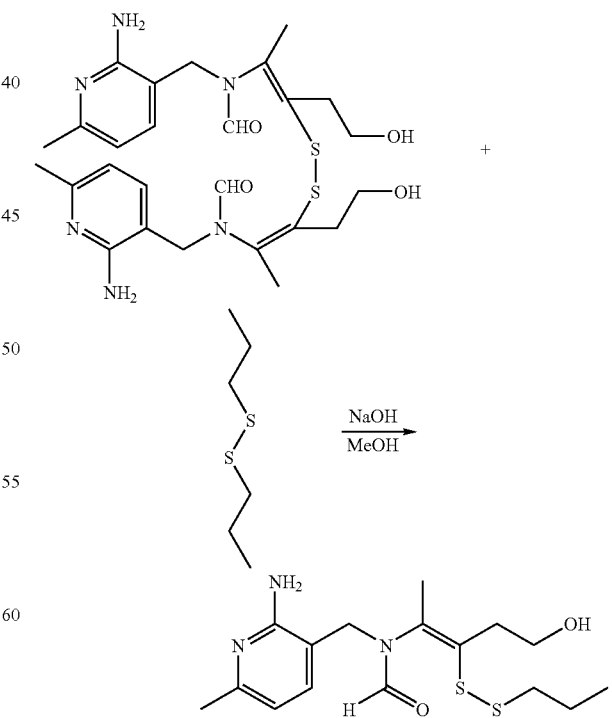

To a solution of N-(2-amino-6-methylpyridin-3-ylmethyl)-N-{2-[2-[(2-amino-6-methyl-pyridin-3-ylmethyl)

formylamino]-1-(2-hydroxyethyl)-propenyldisulfanyl]-4-hydroxy-1-methylbut-1-enyl}formamide (250 mg, 0.45 mmol) and propyl disulfide (0.21 mL, 1.34 mmol) in methanol (3 ml) was added 1 molar aqueous sodium hydroxide (0.089 mL, 0.089 mmol). The resulting solution was stirred at 35-45° C. for 18 hr. The solution was diluted with water (10 mL) and chloroform (10 mL), but the product remained as a milky insoluble layer. Addition of ethyl acetate (10 mL) and methanol (2 mL) resulted in the formation of two clear layers. The product was contained in the lower layer. This layer was washed with brine (10 mL) dried over sodium sulfate, and evaporated. The residual oil was dissolved in chloroform (1 mL) and chromatographed on silica gel (Waters Sep-Pak 5 g column, using 97.5/2.5 chloroform/methanol as eluent, Fraction size 9 mL). Fractions 4-9 were pooled and evaporated to give 130 mg (41%) of the title compound as nearly colorless oil. MS (LCMS): 356.0 (M+H)+. $^1$H NMR (CDCl$_3$) δ 0.95 (t, 3H), 1.55 (m, 3H), 1.97 (s, 3H), 2.35 (s, 3H), 2.42 (t, 2H), 2.84 (t, 2H) 3.76 (t, 2H), 5.36 (br. s, 1H), 6.35 (d, 1H), 7.02 (d, 1H), 7.96 (s, 1H).

Example 3

N-{2-[2-[Acetyl-(2-amino-6-methylpyridin-3-ylmethyl)amino]-1-(2-hydroxyethyl)propenyldisulfanyl]-4-hydroxy-1-methylbut-1-enyl}-N-(2-amino-6-methylpyridin-3-ylmethyl)acetamide (III-14)

3.01 (s, 3H), 3.10 (t, 2H), 4.26 (t, 2H); MS (APCI+) m/z (rel intensity) 200.0 (100).

b) 2-(2,4-Dimethylthiazol-5-yl)ethanol. To a solution of acetic acid 2-(2,4-dimethylthiazol-5-yl) ethyl ester (5 g, 25 mmol) in methanol (100 mL) was added lithium hydroxide monohydrate (1.05 g, 25 mmol) and the reaction was stirred for 1 hour. The solution was concentrated in vacuo and the resulting paste was partitioned between water (100 mL) and dichloromethane (100 mL). The aqueous phase was extracted with dichloromethane and the combined organic phase was dried over magnesium sulfate. Concentration of the organic phase gave 3.2 g (81%) of the title compound as clear oil: $^1$H NMR (CDCl$_3$) δ 1.90 (t, 1H), 2.27 (s, 3H), 2.57 (s, 3H), 2.90 (t, 2H), 3.76 (q, 2H); MS (APCI+) m/z (rel intensity) 158.0 (100).

c) 3-(2-Amino-6-methylpyridin-3-ylmethyl)-5-(2-hydroxyethyl)-2,4-dimethylthiazol-3-ium chloride hydrochloride. 2-(2,4-Dimethylthiazol-5-yl)ethanol (180 mg, 1.1 mmol) and 3-chloromethyl-6-methylpyridin-2-ylamine hydrochloride (Example 1, part (e), 200 mg, 1 mmol) were mixed together in a conical vial and stirred at 60° C. for 20 minutes. While the reaction was still warm, dichloromethane was added and the resulting solid was collected by filtration and dried under vacuum to give 271 mg (83%) of the title compound as a white powder: $^1$H NMR (d$_6$-DMSO) δ 2.34 (s, 3H), 2.45 (s, 3H), 2.95 (s, 3H), 3.03 (t, 2H), 3.66 (t, 2H), 5.69

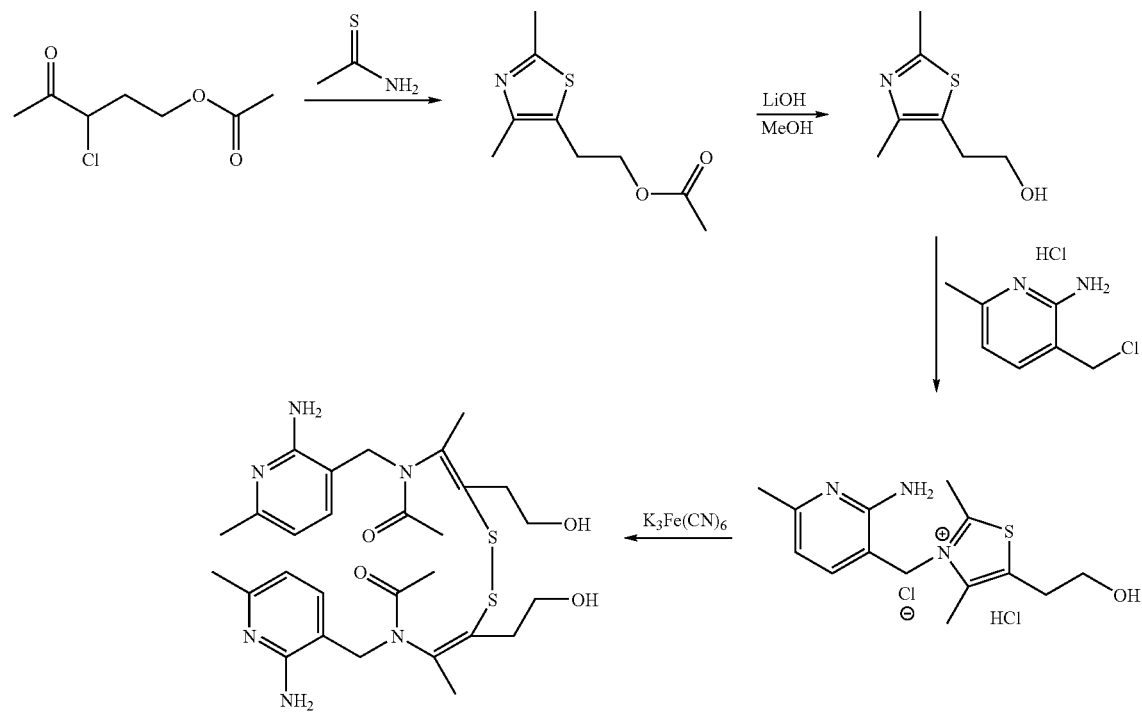

(s, 2H), 6.66 (d, 1H), 7.05 (d, 1H), 8.30 (br s, 1H); MS (APCI+) m/z (rel intensity) 278.0 (60).

a) Acetic acid 2-(2,4-dimethylthiazol-5-yl) ethyl ester. Acetic acid 3-chloro-4-oxo-pentyl ester (prepared from 2-acetylbutyrolactone J. Med. Chem. 1979, 22(3), 306) (4.75 g, 27 mmol) and thioacetamide (2 g, 27 mmol) were heated to 110-120° C. under a stream of nitrogen for 30 minutes. Cooling of the reaction gave 5.3 g (100%) of the title compound as thick tan oil: $^1$H NMR (CDCl$_3$) δ 2.09 (s, 3H), 2.56 (s, 3H), d) N-{2-[2-[Acetyl-(2-amino-6-methylpyridin-3-ylmethyl)amino]-1-(2-hydroxyethyl)propenyldisulfanyl]-4-hydroxy-1-methylbut-1-enyl}-N-(2-amino-6-methylpyridin-3-ylmethyl)acetamide. This compound was prepared according to the procedure of Example 1, part (g), starting from 3-(2- amino-6-methylpyridin-3-ylmethyl)-5-(2-hydroxyethyl)-2,4-dimethylthiazol-3-ium chloride hydrochloride (30 mg, 0.1 mmol). The title compound was isolated as a yellow solid (20 mg, 72%): $^1$H NMR (CDCl$_3$) δ (mixture of cis and trans acetamides) 1.86 (d, 3H), 1.99 (d, 3H), 2.34 (s, 3H), 2.21-2.55 (m, 2H), 3.36-3.62 (m, 2H), 4.20 (dd, 1H), 4.75 (dd, 1H), 5.48 (br. s, 2H), 6.36 (d, 1H), 7.00 (dd, 1H); MS (APCI+) m/z (rel intensity) 589.1 (100).

Example 4

N-(2-Amino-pyridin-3-ylmethyl)-N-{2-[2-[(2-amino-pyridin-3-ylmethyl)-formyl-amino]-1-(2-hydroxy-ethyl)-propenyldisulfanyl]-4-hydroxy-1-methyl-but-1-enyl}-formamide (III-15)

3-(2-amino-pyridin-3-ylmethyl)-5-(2-hydroxy-ethyl)-4-methyl-thiazol-3-ium hydrochloride (200 mg, 0.7 mmol) was treated according to the procedure described for Example 1 (g) to provide the title compound as clear glass (125 mg, 67%): $^1$H NMR (CDCl$_3$) δ 1.99 (s, 3H), 2.43 (t, 2H), 3.50 (t, 2H), 5.42 (br s, 2H), 6.51 (ddd, 1H), 7.11 (ddd, 1H), 7.86 (s, 1H), 7.99 (ddd, 1H); MS (APCI+) m/z (rel intensity) 533.1 (10), 268.0 (40).

Example 5

Determining Inhibition Constants of TPP Mimetics in Cell Free Assay

Purified TK Apo Enzyme

Each compound was first evaluated for its ability to be pyrophosphorylated by thiamine pyrophosphate kinase 1 (TPK1). The reaction was carried out in 50 mM HEPES, 1 mM DTT, 1 mM MgCl$_2$, pH 8.0, 0.1 or 0.5 mM thiamine analog, 4 mM Mg-ATP, 1 mM phosphoenolpyruvate (PEP), 0.6 mM NADH, 5 units of adenylate kinase (AK), pyruvate kinase (PK), and lactate dehydrogenase (LDH), and 46.2 µg of TPK1 in a total volume of 100 µl. The reaction was monitored using absorption spectroscopy at 340 nm using a plate reader. Thiamine was used as a control substrate. A compound was scored as a TPK1 substrate if the slope of the initial rate exceeded 10% of that of thiamine. Compounds scored as TPK1 substrates were then enzymatically converted to pyrophosphate and assessed for an ability to compete with TPP in inhibiting TK activity. The TK inhibition assay was carried out as follows. The pyrophosphorylation reaction mix consisted of 50 mM HEPES, 1 mM DTT, 1 mM MgCl$_2$, pH 8.0, 1 to 10 mM thiamine analog, and 40 mM Mg-ATP. TKP1 (46.2 µg) was added in 10 µL aliquots every hour for 5 hours. The reaction mix was then incubated overnight at 4° C. TPK1 was removed by ultra-filtration using a 10,000 MWCO filter. The extent of reaction was monitored as described above.

The assay used to determine the IC50 of pypophosphorylated compounds 0.025 to 500 µM of the modified compound, 50 mM HEPES, 3 mM DTT, 5 mM MgCl$_2$, 5 mM Na$_2$HAsO$_4$, 0.5 mM NAD$^+$, 5 U/mL of GAPDH, 100 nM TK and 20 µM TPP in a total volume of 50 µL. The above reaction mix (40 µL) was placed in a well of a Costar 3695 half-area plate and pre-incubated at room temperature for 30 min. It was then incubated for 2 minutes at 30° C. The reaction was initiated with the addition of 10 µL pentose phosphates (xylulose 5-phosphate and ribose 5-phosphate) with a final concentration of 0.5 mM. The reaction was monitored at 340 nm using a Molecular Devices Spectramax M2 plate reader. The IC50 values are listed in Table 1 (below).

Example 8

Determining Inhibition Constants of TPP Mimetics in Cellular Assay

Log-phase cells were trypsinized, washed and resuspended in thiamine-free DMEM. Optimization of the initial cell counts was carried out for each cell line prior to IC50 measurements. For cell lines with a doubling time of approximately 24 hours and cellular transketolase levels high enough to be reliably detected with 5,000 cells (such as HCT116 and HT1080), 8,000 cells per well (in a 96-well plate) was found to be satisfactory. Using this initial cell count, IC$_{50}$ could be monitored for six days. Two to four days of treatment resulted in a value that was stable and reproducible.

Media containing 8,000 cells (95 µl) were used to seed individual wells in a 96-well clear-bottom cell cultured-treated sterile plate. Inhibitor compounds were dissolved in 100% DMSO as 10 mM solutions. Serial dilutions were then made in 100% DMSO to make up a 100× stock, then diluted to 20× in double-deionized H2O (ddH2O). Twenty-four hours after seeding, 5 µl of 20× inhibitor compound stock solution was added to the cells so that the final concentration of DMSO was 1%. Media were changed after 24 hours. Forty-eight hours after inhibitor compound treatment, the plates were inverted to remove media and blotted on a paper towel. The plates were then either subjected to enzymatic reactions immediately or were frozen at −20° C. for future assays.

Lysis buffer (20 mM HEPES, pH 7.5, 1 mM EDTA, 0.2 g/l Triton X-100® and 0.2 g/L sodium deoxycholate, supplemented with 1 mM DTT and 1 mM PMSF just before use, 80 µl) were added to each well of the assay plate and allow cell lysis at RT with shaking. Then 15 ul of 5× assay buffer containing final concentrations of 50 mM HEPES, 40 mM KCl, 2.5 mM MgCl2, 5 mM NaArsenate, 1 mM NAD, 2 unit/ml glyceraldehyde-3-phosphate dehydrogenase (GAPDH) was added to the 80 ul of lysate. Reaction kinetics were monitored on a fluorescent plate reader to allow any possible background activity via GAPDH to burn out. Then 5 ul of substrate mix containing final concentrations of 0.5 mM ribose-5-phosphate and 0.5 mM xylulose-5-phosphate was added to initiate the reaction. Monitor reaction kinetics were monitored using a fluorescent plate reader and the slope of the initial linear range was recorded as the velocity of the reaction (FU/min). Enzymatic inhibition was expressed as percent of control wells that were not treated with compounds. The values (y) were plotted as function of the log concentration (x) and fitted to a sigmoidal dose-response curve with variable slopes that bears the equation: y=bottom+(top−bottom)/(1+10^((log EC50-x)*hillslope)). The IC50 values for colon carcinoma HCT116 are listed in Table 1 (below)

TABLE 1

Inhibition Constants of TPP Mimetics

| STRUCTURE | TPK-apoTK IC$_{50}$ (nM) | HCT116 TK IC$_{50}$ (nM, mean) |
|---|---|---|
| (structure 1) | 88.80 | 25 |
| (structure 2) | Not a Substrate ("NS") | 1040 |
| (structure 3) | NS | 253 |
| (structure 4) | 10.13 | 24 |
| (structure 5) |  | 13 |

TABLE 1-continued

Inhibition Constants of TPP Mimetics

| STRUCTURE | TPK-apoTK IC$_{50}$ (nM) | HCT116 TK IC$_{50}$ (nM, mean) |
|---|---|---|
| (structure) | NS | 52 |
| (structure) | 117.05 | 198 |
| (structure) | | 70 |
| (structure) | | 7730 |
| (structure) | NS | 102000 |

TABLE 1-continued

Inhibition Constants of TPP Mimetics

| STRUCTURE | TPK-apoTK IC$_{50}$ (nM) | HCT116 TK IC$_{50}$ (nM, mean) |
|---|---|---|
| 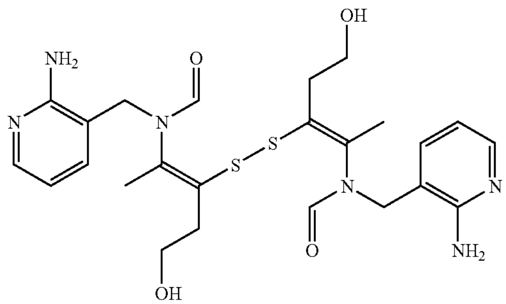 | NS | 479 |
| 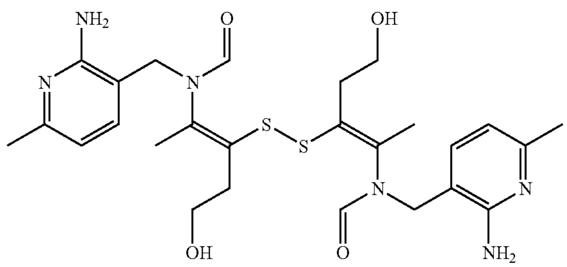 | 803.23 | 10 |
| 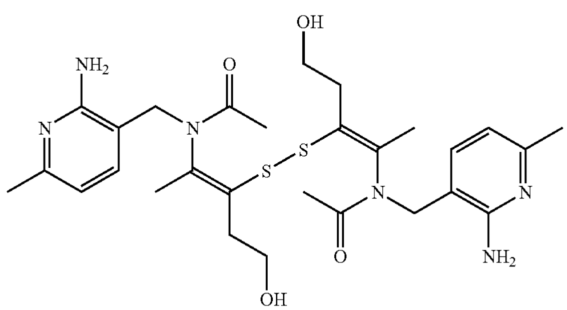 | 214.25 | 32 |
| | | 8 |

TABLE 1-continued

Inhibition Constants of TPP Mimetics

| STRUCTURE | TPK-apoTK IC$_{50}$ (nM) | HCT116 TK IC$_{50}$ (nM, mean) |
|---|---|---|
| 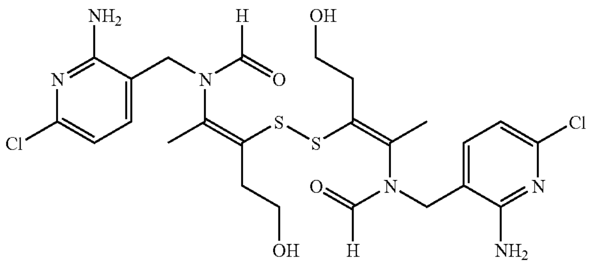 | 30.90 | 5.27 |
| | NS | 6460 |
| | NS | 3702 |
| | NS | 1870 |
| | NS | |

TABLE 1-continued

Inhibition Constants of TPP Mimetics

| STRUCTURE | TPK-apoTK IC$_{50}$ (nM) | HCT116 TK IC$_{50}$ (nM, mean) |
|---|---|---|
| (structure) | NS | 116 |
| (structure) |  | 25 |
| (structure) | NS | 50 |
| (structure) |  | 507 |
| (structure) |  | 26350 |

TABLE 1-continued

Inhibition Constants of TPP Mimetics

| STRUCTURE | TPK-apoTK IC$_{50}$ (nM) | HCT116 TK IC$_{50}$ (nM, mean) |
|---|---|---|
| | NS | 19435 |
| | NS | 2478 |
| | NS | |
| | | 50 |

TABLE 1-continued

Inhibition Constants of TPP Mimetics

| STRUCTURE | TPK-apoTK IC$_{50}$ (nM) | HCT116 TK IC$_{50}$ (nM, mean) |
|---|---|---|
| (structure) | NS | 108 |
| (structure) | NS | 28 |
| (structure) | NS | 7160 |
| (structure) | NS | 15 |

"TPK-TK" in the second column in Table 1 designates the thiamine pyrophosphate kinase/transketolase coupled reaction.

What is claimed is:

1. A compound of formula I:

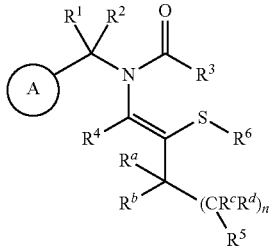

or a pharmaceutically acceptable salt, stereoisomer, enantiomer, or tautomer thereof, wherein:

ring A is optionally substituted and is

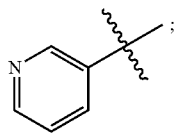

each $R^1$ and $R^2$ is independently H, alkyl, or fluoroalkyl;
$R^3$ is H, alkyl, fluoroalkyl, aralkyl, carbocyclylalkyl, heterocyclyl, carbocyclyl, heterocyclylalkyl, aryl, heteroaryl, heteroaralkyl, —C(O)R, —OR, —(CH$_2$)$_{1-6}$OR, —(CH$_2$)$_{1-6}$N(R)$_2$, —N(R)$_2$, or —C(H)(OR)R;
$R^4$ is H, alkyl, fluoroalkyl, —CO$_2$R, —CON(R)$_2$, carbocyclyl, carbocyclylalkyl, heteroaryl, or heterocyclyl;
$R^5$ is —OR$^7$ or —NR$^8$R$^9$;
$R^6$ is —C(O)R, —C(S)R, —C=C—C(O)R, —SR, —S—W—OR$^7$, or Y;

Y is

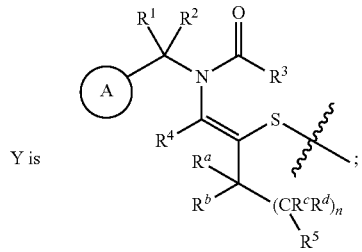

$R^7$ is R$^o$, —C(O)R, —C(O)N(R)$_2$, —C(O)OR, —(CH$_2$)$_{1-6}$—C(O)R, —PO$_3$M$_x$, —P(O)(alkyl)OM', —(PO$_3$)$_2$M$_y$, carbocyclyl, aryl, heterocyclyl, heteroaryl, carbocyclylalkyl, aralkyl, heterocyclylalkyl, or heteroaralkyl;
x is 1 or 2;
y is 1, 2 or 3;
each M is independently H, Li, Na, K, Mg, Ca, Mn, Co, Ni, Zn, or alkyl;
M' is H, Li, Na, K, or alkyl;
$R^8$ is H or alkyl;
$R^9$ is H, alkyl, —C(O)R, —C(O)N(R)$_2$, —C(O)OR, —SO$_2$R, —SO$_2$N(R)$_2$, carbocyclyl, aryl, heterocyclyl, heteroaryl, carbocyclylalkyl, aralkyl, heterocyclylalkyl, or heteroaralkyl;
each $R^a$ and $R^b$ is independently H, OR$^o$, alkyl, or fluoroalkyl;
each $R^c$ and $R^d$ is independently H, alkyl, or fluoroalkyl;
n is 0-4;
W is alkylene, arylene, heteroarylene, carbocyclylene, or heterocyclylene;
$R^o$ is H or alkyl; and
R is R$^o$, carbocyclyl, aryl, heterocyclyl, heteroaryl, carbocyclylalkyl, aralkyl, heterocyclylalkyl, or heteroaralkyl.

2. The compound of claim 1, wherein $R^6$ is Y or —SR.

3. The compound of claim 1, wherein:
   i) $R^1$, $R^2$ and $R^4$ are independently H, C$_{1-6}$ alkyl or fluoro (C$_{1-6}$ alkyl);
   ii) $R^3$ is H, alkyl, fluoroalkyl, —(CH$_2$)$_{1-6}$OR, —(CH$_2$)$_{1-6}$N(R)$_2$, —C(O)R, —C(H)(OR)R, aralkyl, heterocyclyl, heterocyclylalkyl, heteroaryl, or heteroaralkyl;
   iii) $R^6$ is —C=C—C(O)R, —SR, —S—W—OR$^7$, or Y;
   iv) $R^7$ is H, alkyl, —C(O)R, —PO$_3$M$_x$, —(PO$_3$)$_2$M$_y$, —P(O)(alkyl)OM', —C(O)N(R)$_2$, or —C(O)OR; or $R^9$ is H, alkyl, —C(O)R, —C(O)N(R)$_2$, —C(O)OR, —SO$_2$R, 5-membered heterocyclyl, or a 5-membered heteroaralkyl; and
   v) n is 1.

4. The compound of claim 3, wherein R is R$^o$, carbocyclyl, aryl, heteroaryl, heterocyclyl, aralkyl, heterocyclylalkyl or heteroaralkyl.

5. The compound of claim 4, wherein R$^o$ is H or C$_{1-6}$ alkyl.

6. The compound of claim 3, wherein:
   i) ring A is optionally substituted with —NH$_2$, alkyl, —OC(O)R$^†$, halo, —OR$^†$, —CF$_3$, —OCF$_3$, —SCF$_3$, —SR$^†$, —R$^†$, —NR$^†$C(O)R$^†$, —CO$_2$R$^†$, —NO$_2$, —N(R$^†$)$_2$, —CN, —C(O)R$^†$, —C(O)N(R$^†$)$_2$, —SO$_2$N(R$^†$)$_2$, —NR$^†$CO$_2$R$^†$, —C(O)C(O)R$^†$, —OC(O)N(R$^†$)$_2$, —S(O)$_z$R$^†$, —C(O)CH$_2$C(O)R$^†$, —NR$^+$SO$_2$R$^†$, or —C(=S)N(R$^†$)$_2$; and R$^†$ is 3-6 membered unsubstituted cycloalkyl, phenyl, benzyl, naphthyl, pyridyl, or C$_{1-6}$ alkyl optionally substituted with halo;
   ii) $R^3$ is H, C$_{1-6}$ alkyl, —(CH$_2$)$_{1-6}$OR$^o$ or —CH(OR$^o$)R$^o$;
   iii) $R^6$ is —C=C—C(O)R, —SR, —S—W—OR$^7$ or Y; and
   iv) $R^8$ is H or C$_{1-6}$ unsubstituted alkyl.

7. The compound of claim 6, wherein $R^7$ or $R^9$ is H or

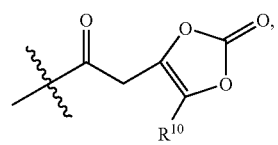

wherein $R^{10}$ is H, alkyl, or aryl.

8. The compound of claim 6, wherein:
   i) $R^1$, $R^2$ and $R^4$ are independently H, methyl, ethyl, —CH$_2$F, —CHF$_2$, or —CF$_3$;
   ii) $R^3$ is H, methyl, ethyl, —CH(OH)CH$_3$, —CH$_2$OH, or —CH$_2$CH$_2$OH;
   iii) $R^6$ is —S-(heterocyclylalkyl), (—S-(unsubstituted C$_{1-6}$ alkyl), Y,

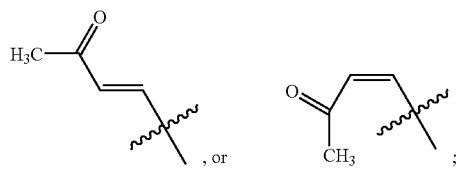
iv) R⁸ is H, methyl, or ethyl;
v) R⁷ is H, methyl, ethyl, —C(O)Me, —C(O)Et, —C(O)NMe₂, —C(O)-p-OMe-phenyl, —C(O)O-phenyl, —PO₃H₂, —P(O)(OMe)₂, —P(O)(OMe)OH, —P(O)(Me)OH, or —P(O)(OH)OP(O)(OH)(OH) and
vi) R⁹ is H, methyl, ethyl,
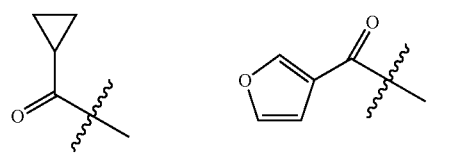
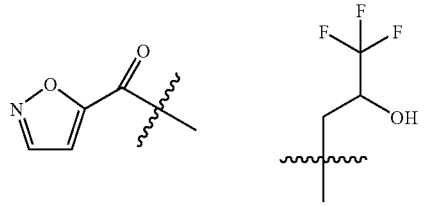
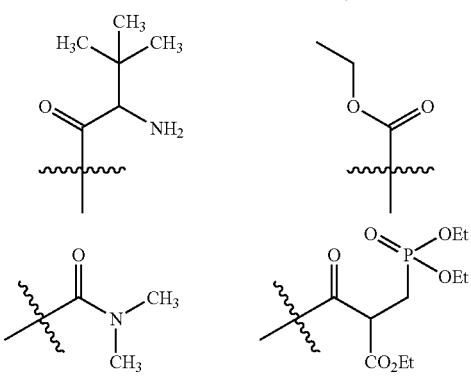
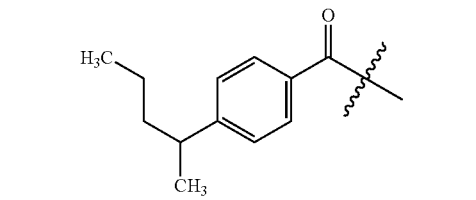
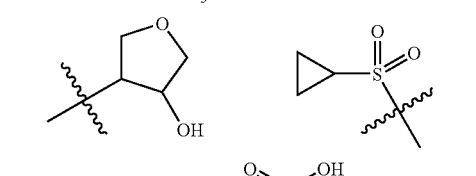
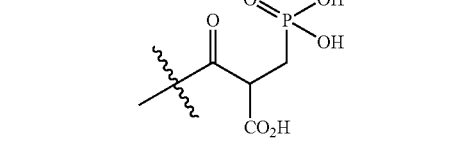
-continued
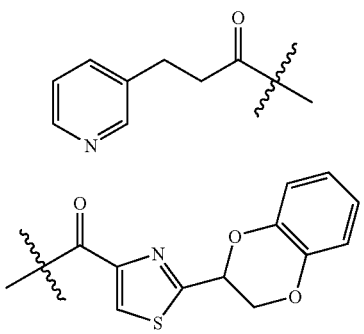
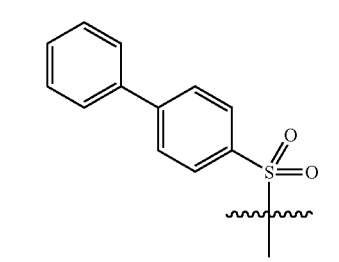
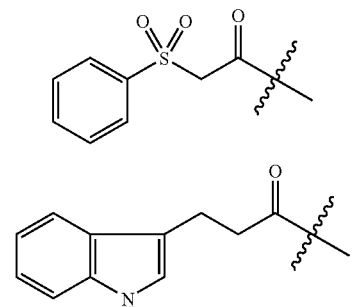
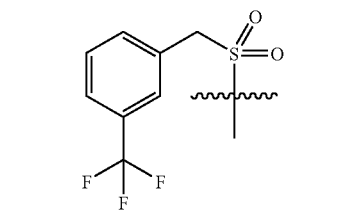
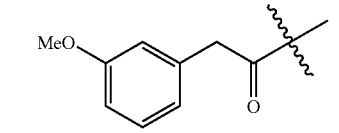
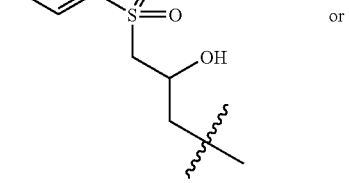
or
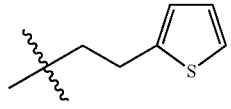

-continued

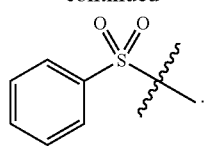

9. The compound of claim 1, wherein said compound is selected from the group consisting of the compounds of:

(1) formula IIa:

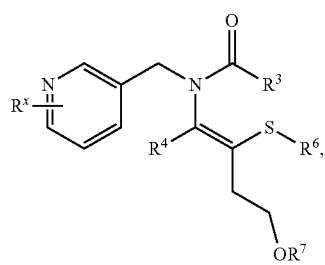

where $R^3$ and $R^4$ are independently H or alkyl, $R^6$ is —SR, $R^7$ is $R^o$, and $R^x$ can be the same or different and is selected from the group consisting of alkyl and $NH_2$;

(2) formulae III:

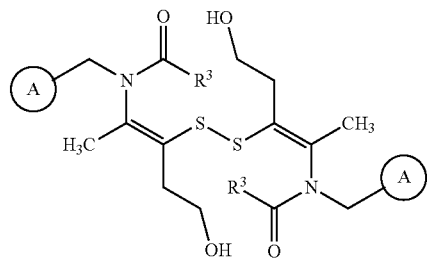

where A is

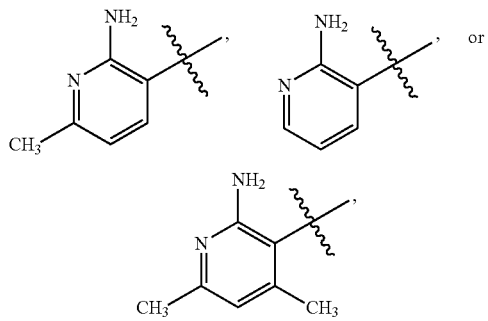

and $R^3$ is H or $CH_3$; and (3) formulae IV:

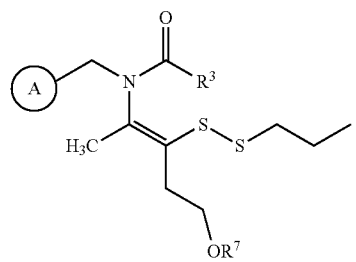

where A is

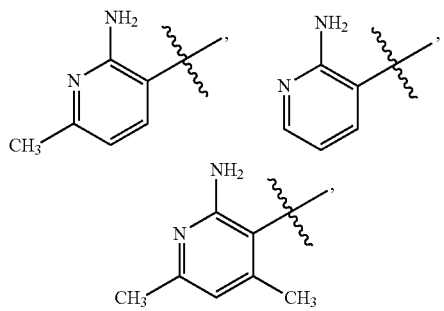

and $R^3$ is H or $CH_3$.

10. A pharmaceutical composition comprising a compound of claim 1 and a pharmaceutically acceptable carrier.

11. A compound of the formula:

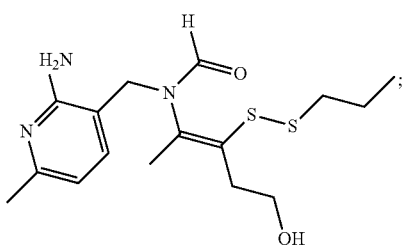

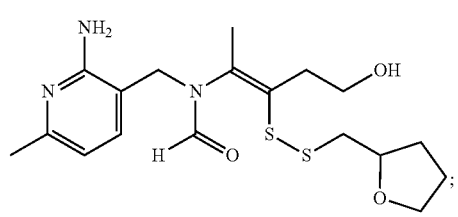

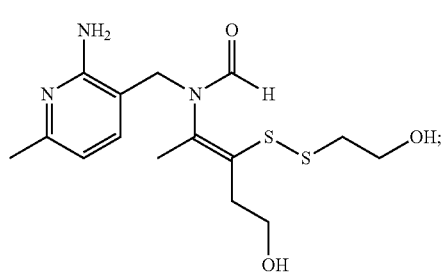

(d) 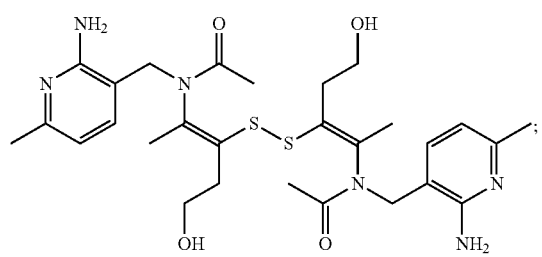
(e) 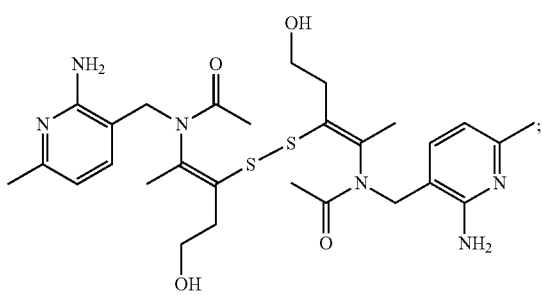
(f) 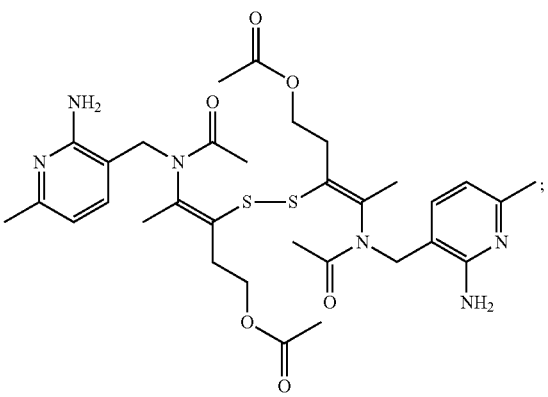
(g) 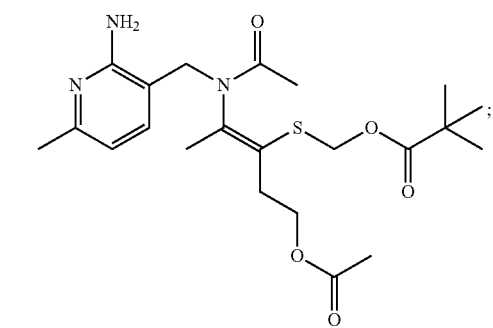
(h) 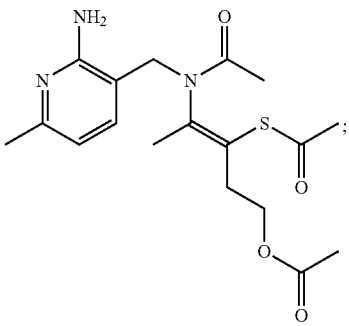
(i) 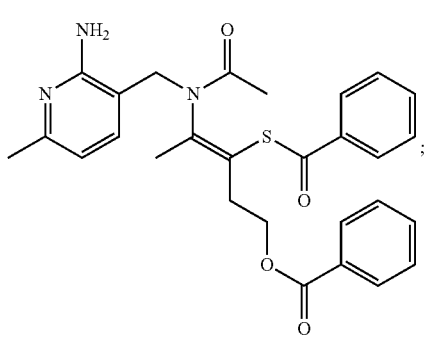
(j) 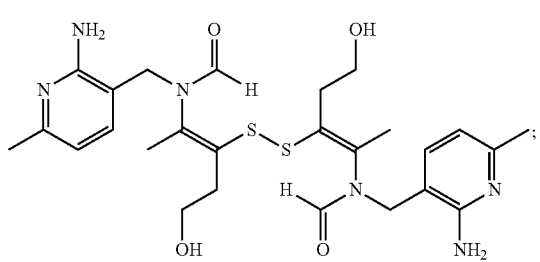
(k) 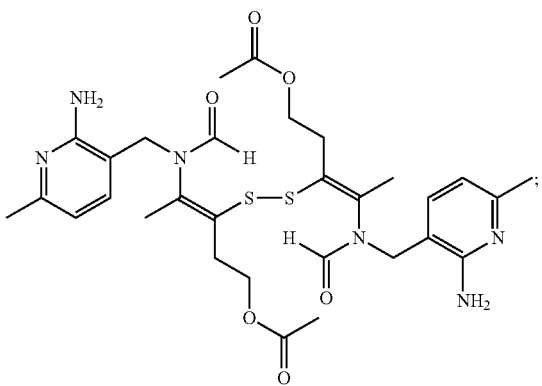

-continued

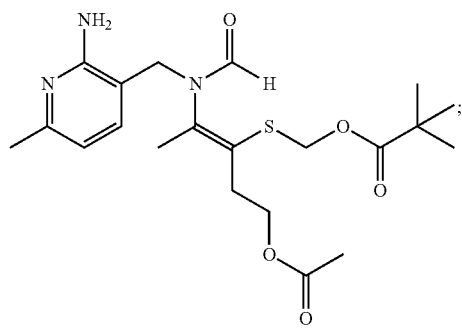
(l)

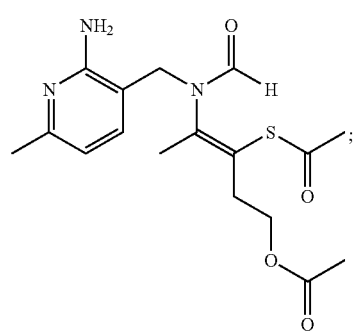
(m)

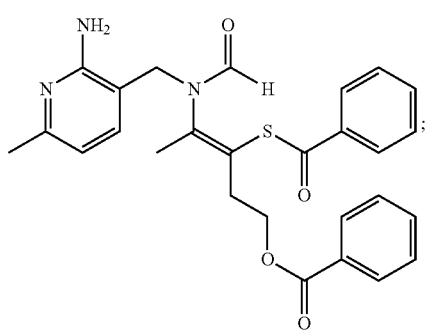
(n)

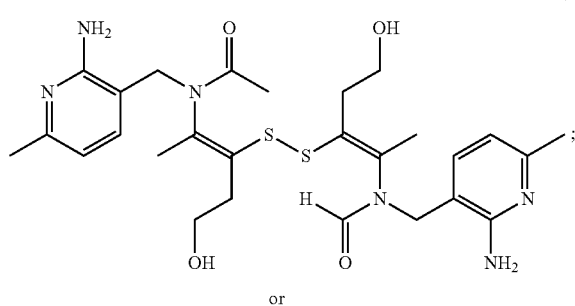
(o)

or

-continued

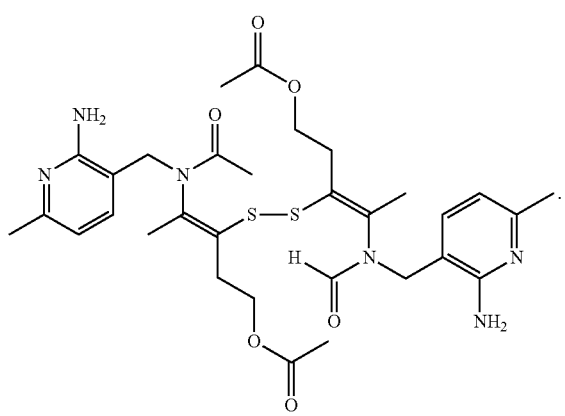
(p)

or a pharmaceutically acceptable salt, stereoisomer, enantiomer, or tautomer thereof.

12. The compound of claim 11, wherein the compound is:

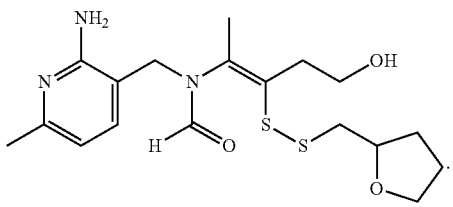

13. A compound of the formula

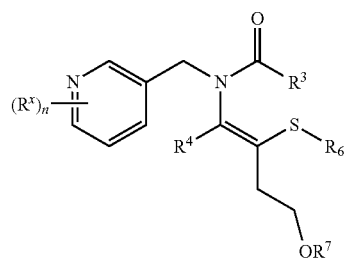

or a pharmaceutically acceptable salt, ester, stereoisomer, enantiomer, or tautomer thereof, wherein:
(a) $R^3$ and $R^4$ may each be the same or different to the extent they occur more than once in the compound and are independently H or alkyl;
(b) $R^7$ may be the same or different to the extent it occurs more than once in the compound and is independently $R^o$ or —C(O)R, where $R^o$ is H or alkyl and R is $R^o$, carbocyclyl, aryl, heterocyclyl, heteroaryl, carbocyclalkyl, aralkyl, heterocyclylalkyl, or heteroaralkyl;
(c) $R^x$ may be the same or different to the extent it occurs more than once in the compound and is independently alkyl or $NH_2$;
(d) $R^6$ is —SR, —C(O)R,

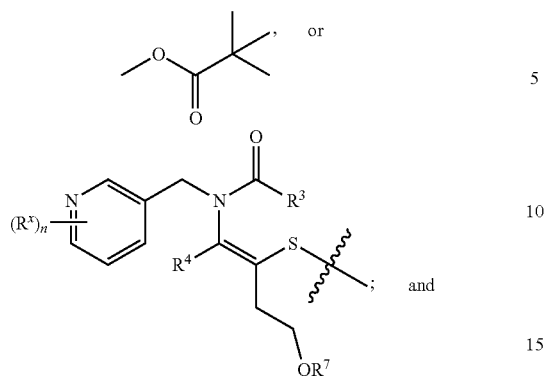
(e) n is 0, 1, 2, or 3.
* * * * *